United States Patent [19]

Baldwin et al.

[11] Patent Number: 4,797,413

[45] Date of Patent: * Jan. 10, 1989

[54] THIENO THIOPYRAN SULFONAMIDE DERIVATIVES, PHARMACEUTICAL COMPOSITIONS AND USE

[75] Inventors: John J. Baldwin, Gwynedd Valley; Gerald S. Ponticello, Lansdale; Marcia E. Christy, Collegeville, all of Pa.

[73] Assignee: Merck & Co., Inc., Rahway, N.J.

[ * ] Notice: The portion of the term of this patent subsequent to Jun. 30, 2004 has been disclaimed.

[21] Appl. No.: 67,326

[22] Filed: Jun. 26, 1987

Related U.S. Application Data

[63] Continuation-in-part of Ser. No. 863,225, May 14, 1986, Pat. No. 4,677,115, which is a continuation-in-part of Ser. No. 777,654, Sep. 19, 1985, abandoned, which is a continuation-in-part of Ser. No. 680,684, Dec. 12, 1984, abandoned.

[51] Int. Cl.$^4$ .................. A61K 31/38; A61K 31/535; C07D 495/04

[52] U.S. Cl. .................. 514/432; 514/232.5; 514/233.8; 514/253; 514/316; 514/318; 514/321; 514/338; 514/422; 514/913; 544/79; 544/121; 544/130; 544/131; 544/141; 544/145; 544/146; 544/357; 544/364; 544/372; 544/377; 546/187; 546/193; 546/194; 546/197; 546/220; 548/523; 548/526; 549/23

[58] Field of Search ............ 549/23; 514/431, 432, 514/232.5, 233.8, 253, 316, 318, 321, 338, 422; 544/79, 121, 130, 131, 141, 145, 146, 357, 364, 372, 377; 546/187, 193, 194, 197, 270; 548/523, 526

[56] References Cited

U.S. PATENT DOCUMENTS

| | | | |
|---|---|---|---|
| 4,092,325 | 5/1978 | Sircar et al. | 260/307 |
| 4,542,152 | 9/1985 | Shepard | 514/445 |
| 4,668,697 | 5/1987 | Shepard et al. | 514/443 |
| 4,677,115 | 6/1987 | Baldwin et al. | 514/432 |

FOREIGN PATENT DOCUMENTS

| | | | |
|---|---|---|---|
| 182691 | 10/1986 | European Pat. Off. | 514/432 |
| 228237 | 7/1987 | European Pat. Off. | 514/432 |

*Primary Examiner*—Robert W. Ramsuer
*Attorney, Agent, or Firm*—William H. Nicholson; Michael C. Sudol, Jr.

[57] ABSTRACT

Aromatic sulfonamides with a saturated heterocycle fused thereto are carbonic anhydrase inhibitors useful in the treatment of elevated intraocular pressure.

13 Claims, No Drawings

THIENO THIOPYRAN SULFONAMIDE DERIVATIVES, PHARMACEUTICAL COMPOSITIONS AND USE

SUMMARY OF THE INVENTION

This is a continuation-in-part of copending application Ser. No. 863,225 filed May 14, 1986, now U.S. Pat. No. 4,677,115, which in turn is a continuation-in-part of copending application Ser. No. 777,654, filed Sept. 19, 1985 (now abandoned) which in turn is a continuation-in-part of application, Ser. No. 680,684, filed Dec. 12, 1984 (now abandoned).

This invention relates to novel aromatic sulfonamides useful in the treatment of elevated intraocular pressure. More particularly this invention relates to compounds having the structural formula:

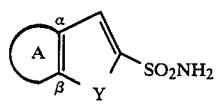

wherein A and Y are as hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino--[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

DETAILED DESCRIPTION OF THE INVENTION

The novel compounds of this invention are those with structural formula:

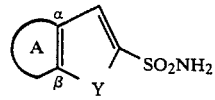

One embodiment of the compounds is the class of compounds wherein A together with the two carbon atoms denoted as $\alpha$ and $\beta$ is the group:

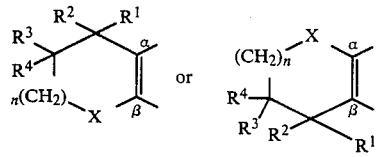

wherein:

X is —S—, —SO—, —SO$_2$— or —CH$_2$—;

Y is —S—, —O—, or —NR$^3$— wherein R$^3$ is hydrogen, C$_{1-3}$alkyl, or benzyl;

n is 1 or 2;

R$^1$, R$^2$, R$^3$, R$^4$ are independently selected from:
(1) hydrogen,
(2) OR$^5$ wherein R$^5$ is:
 (a) hydrogen,
 (b) C$_{1-5}$ alkyl, either unsubstituted or substituted with —OH, or

wherein R$^6$ and R$^7$ are independently hydrogen or C$_{1-5}$ alkyl, or joined together form a heterocycle with the nitrogen to which they are attached such as piperidino, morpholino, or piperazino,
(c) C$_{1-5}$ alkanoyl, either unsubstituted or substituted with —OH, —NR$^6$R$^7$, —NH—COR$^8$ or —COR$^8$ wherein R$^8$ is —OH, —NR$^6$R$^7$ or C$_{1-5}$ alkoxy,
(d) —CO—R$^9$, wherein R$^9$ is —NR$^6$R$^7$ or a 5- or 6-membered aromatic heterocycle such as pyridyl, imidazolyl, pyrazinyl, thiazolyl, thienyl, or oxazolyl,
(3) —NR$^6$R$^7$,
(4) —NHR$^{10}$ wherein R$^{10}$ is:
  (a) —SO$_2$NR$^6$R$^7$,
  (b) —SO$_2$R$^{11}$, wherein R$^{11}$ is C$_{1-5}$ alkyl, or
  (c) —CONR$^6$R$^7$,
(5) C$_{1-5}$ alkyl, either unsubstituted or substituted with
  (a) —OR$^5$,
  (b) —CN,
  (c) —NR$^6$R$^7$, or
  (d) —COR$^8$,
(6) —SO$_2$R$^{11}$,
(7) —SO$_2$NR$^6$R$^7$, or
(8) —halo, such as chloro, bromo or fluoro;
R$^1$ and R$^3$, or R$^2$ and R$^4$ taken together represent a double bond;
R$^1$ and R$^2$, or R$^3$ and R$^4$ taken together represent
  (1) =O, or
  (2) =NOR$^{12}$ wherein R$^{12}$ is hydrogen or C$_{1-3}$alkyl; and
one of the —CH$_2$— groups of —(CH$_2$)$_n$— can be substituted with —COR$^8$, —CH$_2$R$^8$, or —CH$_2$COR$^8$.

It is preferred that Y is —S. It is also preferred that X is —S— or —SO$_2$—, n is 1, R$^2$ is hydrogen, R$^3$ and R$^4$ are hydrogen or C$_{1-5}$ alkyl and R$^1$ is —OH, —CH$_2$OH or —NR$^6$R$^7$.

Another embodiment of the novel compounds of this invention are those with structural formula:

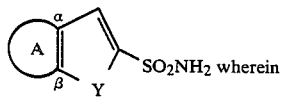SO$_2$NH$_2$ wherein

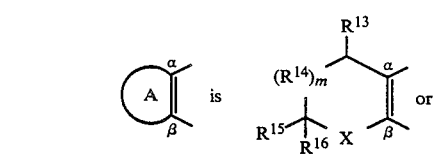 is 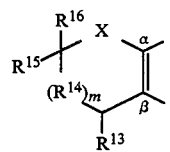 or wherein:
X is —S—, —SO$_2$, —SO$_2$— or —CH$_2$—;
Y is —S—, —O—, or —NR$^{19}$, wherein R$^{19}$ is H, C$_{1-3}$alkyl or benzyl,
R$^{13}$ is
  (a) hydrogen,
  m is 0 or 1
  (b) phenyl either unsubstituted or substituted with one or more of
    (b 1) hydroxy,
    (2) C$_{1-3}$alkoxy,
    (3) R$^{17}$R$^{18}$N-C$_{1-5}$alkyl wherein R$^{17}$ and R$^{18}$ are independently selected from:
      (i) hydrogen or
      (ii) C$_{1-5}$alkyl, or taken together with the nitrogen to which they are attached form a heterocycle such as morpholine, piperidine, pyrrolidine, or piperazine,
  (c) —OH,
  (d) =O; or
  (e) —NR$^{17}$R$^{18}$
R$^{14}$ is
  (a) hydrogen,
  (b) —CN,
  (c) phenyl-C$_{1-3}$-alkyl, wherein the phenyl is either unsubstituted or substituted with one or more of
    (1) hydroxy,
    (2) C$_{1-3}$alkoxy, or
    (3) R$^{17}$R$^{18}$N-C$_{1-5}$alkyl;
R$^{15}$ is (a) hydrogen,
  (b) C$_{1-5}$alkyl,
  (c) phenyl-C$_{1-3}$alkyl, wherein the phenyl is either unsubstituted or substituted with one or more of:
    (1) hydroxy,
    (2) C$_{1-3}$alkoxy,
    (3) R$^{17}$R$^{18}$N-C$_{1-3}$alkyl;
  (d) phenyl either unsubstituted or substituted with one or more of
    (1) hydroxy,
    (2) C$_{1-3}$alkoxy,
    (3) R$^{17}$R$^{18}$N-C$_{1-3}$alkyl, or
    (4) halo, such as chloro or fluoro
  (e) aromatic heterocycle of 5 or 6 members such as furyl, pyridyl, or thienyl either unsubstituted or substituted with R$^{17}$R$^{18}$N-C$_{1-3}$alkyl,
  (f) —NR$^{17}$R$^{18}$, and
  (g) C$_{2-5}$alkyl substituted with —NR$^{17}$R$^{18}$;
R$^{16}$ is
  (a) hydrogen,
  (b) C$_{1-3}$alkyl, or
  (c) C$_{1-3}$alkylene, such as methylene;
with the proviso that if R$^{13}$ is other than phenyl or substituted phenyl, and R$^{14}$ is hydrogen, one of R$^{15}$ and R$^{16}$ is other than hydrogen.

It is preferred that X is —SO$_2$—; R$^{13}$ is H or —NR$^{17}$R$^{18}$; R$^{14}$ is hydrogen; R$^{16}$ is hydrogen or C$_{1-3}$ alkyl; and R$^{15}$ is C$_{1-3}$ alkyl or phenyl substituted with hydroxy and/or R$^{17}$R$^{18}$N-C$_{1-3}$ alkyl.

Substitution at R$^{13}$, R$^{14}$, R$^{15}$ or R$^{16}$ may result in compounds with asymmetric carbons. This invention contemplates all of the enantiomers, and diastereomers and mixtures thereof.

Compounds of formula I which are especially preferred are:
5,6-dihydro-4-ethylamino-6-methyl-4H-thieno[2,3-b]thiopyran-2-sulfonamide-7,7-dioxide and its (—)-trans-enantiomer;
5,6-dihydro-4-(2methylpropylamino)-6-methyl-4H-thieno[2,3-b]thiopyran-2-sulfonamide-7,7-dioxide and its (—)-trans-enantiomer;
5,6-dihydro-6,6-dimethyl-4-ethylamino-4H-thieno[2,3-b]thiopyran-2-sulfonamide-7,7-dioxide;
5,6-dihydro-5-(3-dimethylaminomethyl-4-hydroxybenzyl)-4H-thieno[2,3-b]thiopyran-2-sulfonamide-7,7-dioxide; and
5,6-dihydro-6-(3-dimethylaminomethyl-4-hydroxyphenyl)-4H-thieno[2,3-b]thiopyran-2-sulfonamide-7,7-dioxide.

The thieno-dihydrothiopyran ring systems are prepared following the reaction scheme outlined below:

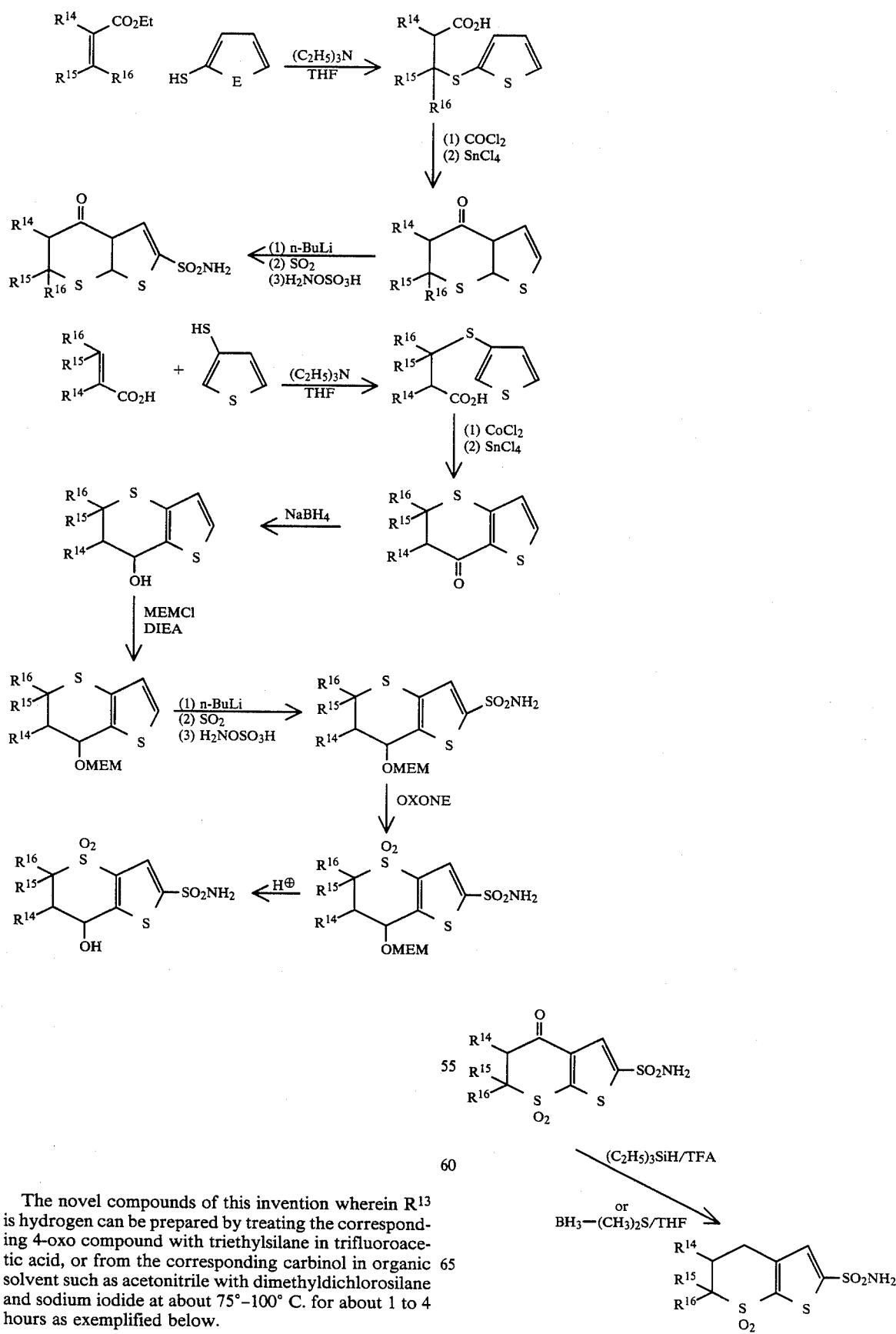
The novel compounds of this invention wherein $R^{13}$ is hydrogen can be prepared by treating the corresponding 4-oxo compound with triethylsilane in trifluoroacetic acid, or from the corresponding carbinol in organic solvent such as acetonitrile with dimethyldichlorosilane and sodium iodide at about 75°–100° C. for about 1 to 4 hours as exemplified below.

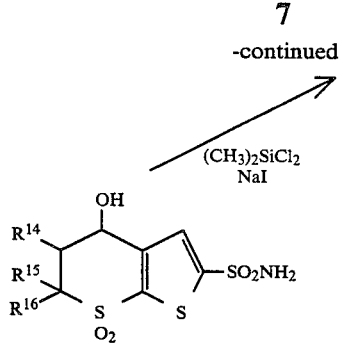

Reduction of the oxo compound is best conducted in an inert atmosphere by adding triethylsilane dropwise to a solution of the ketone in the trifluoroacetic acid (TFA) at room temperature. The triethylsilane and ketone are used in a molar ratio of about 3:1 to 5:1 preferably 4:1. The mixture is heated at about 60° C. to reflux for about 2 to 6 hours. After cooling the excess TFA is neutralized by addition of aqueous base such as sodium bicarbonate. The aqueous solution is extracted with an inert organic solvent such as ethyl acetate and the extract is dried and evaporated to dryness.

Alternatively, reduction of the oxo compound is also accomplished using boranedimethylsulfide in THF as solvent and heating the mixture at reflux for about 3 hours.

The carbinol is reduced by heating at reflux with the dimethyldichlorosilane and NaI in acetonitrile for about 0.5 to 4 hours followed by quenching with water.

The 7,7-dioxide group in most of the novel compounds is generated by treating a $C_{1-3}$alkanolic, preferably methanolic, solution of the corresponding thiopyran with aqueous OXONE®

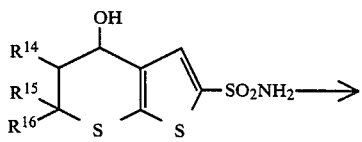

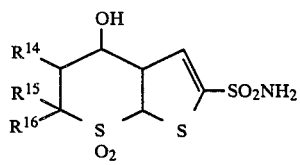

at about room temperature for about 12 to 24 hours.

The 4-hydroxy group present in the thiopyran ring of some of the novel compounds is prepared by reduction of the corresponding 4-keto group with a complex metal hydride, such as sodium borohydride. The reduction is conducted in a $C_{1-3}$alkanol, preferably ethanol at about room temperature for about 0.5 to 3 hours.

A free 4-amino group is achieved by hydrolysis of an N-acyl group such as acetyl with a strong acid such as hydrochloric acid in an aqueous alcohol, preferably methanol at about 75° C. to reflux for about 12 to 24 hours.

Reduction of the N-acyl group with boranedimethylsulfide complex in an ethereal solvent such as THF, diethylether, or 1,2-dimethoxyethane provides an alkylamino as exemplified below by reduction of acetamido to ethylamino. The amide starting materials can be prepared by acylation of the 4-amino compounds.

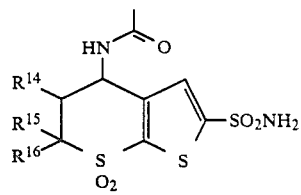

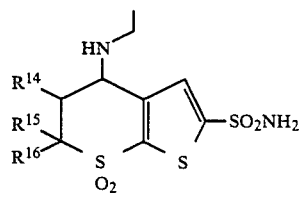

Alkylamino groups are also available from the corresponding 4-hydroxy compounds by treatment of the 4-hydroxy with toluenesulfonyl chloride in pyridine at about −20° C. to 5° C. for about 3 to 10 hours followed by the addition of an alkylamine at a temperature below about 15° C. followed by warming to about 30°–60° C. for about 5 to 16 hours as shown below:

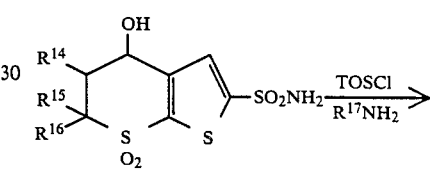

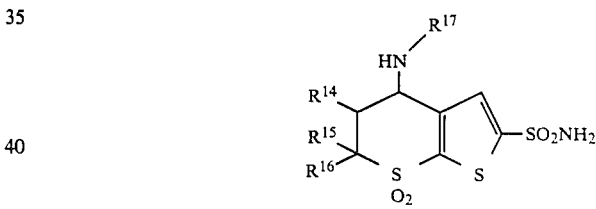

4-Alkylamines are also prepared from the 4-oxo compounds by the following scheme:

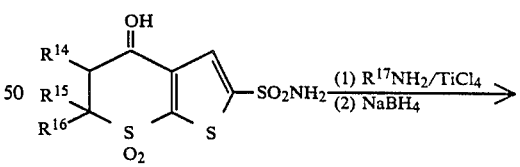

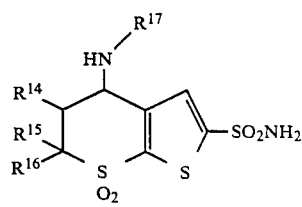

In this process a solution of the keto compound in a solvent such as diethylether, THF, 1,2-dimethoxyethane, benzene, toluene or mixtures thereof at about −20° C. to 0° C. is treated quickly with about a one molar excess of an amine of formula $R^{17}NH_2$ followed by titanium tetrachloride dropwise. After about 1 to 5 hours the mixture is filtered and evaporated. The residue is treated with a complex metal hydride, such as sodium borohydride, in excess in a $C_{1-3}$alkanol, preferably methanol, at about room temperature for up to 24 hours. Excess hydride is destroyed with aqueous acid and the product is isolated by standard techniques.

Aromatic ethers are cleaved by standard procedures such as with boron tribromide, pyridine.HCl, $C_2H_5S\theta$ or the like.

Aromatic dimethylaminomethyl substituents are prepared by standard Mannich reaction procedures.

Compounds with an aminoalkyl function on the carbon adjacent the thiopyran sulfur can be prepared by reduction of the carboxamide to the 6-substituted aminomethyl group followed by oxidation of the sulfur to the 7,7-dioxide.

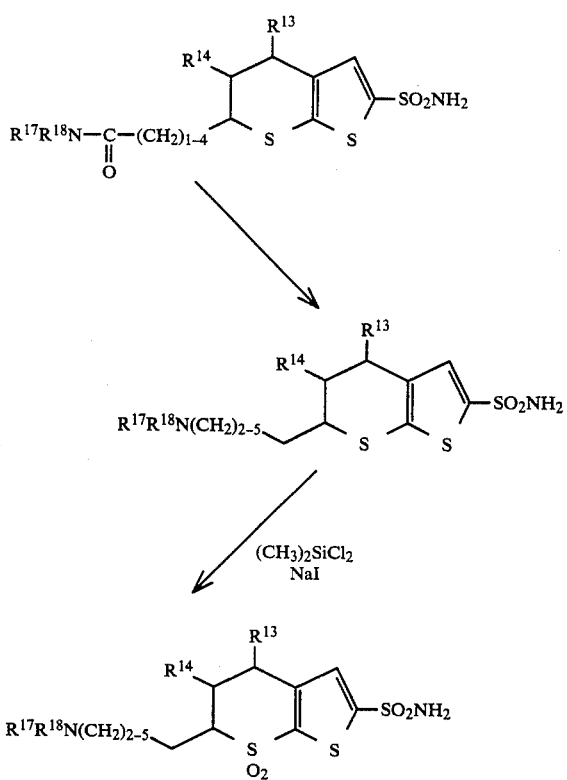

The synthesis of 6-$R^{17}R^{18}$-N-methyl-5,6-dihydro-4H-thieno[2,3-b]thiopyrans via addition of amines to the methylene group of 5,6-dihydro-6-methylene-4H-thieno[2,3-b]thiopyran-2-sulfonamides is illustrative of a general procedure for the preparation of a variety of analogs as outlined below.

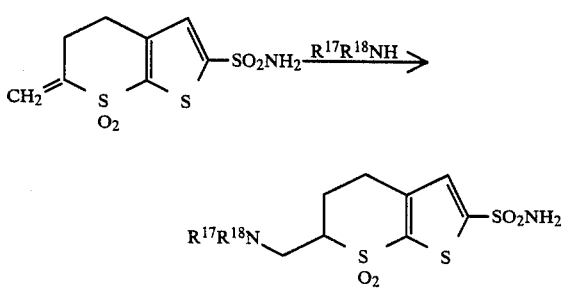

The process comprises mixing the two reagents in a $C_{1-3}$ alkanol, preferably methanol and agitating the mixture at about 12° to 30° preferably about room temperature for about 5 to 24 hours, preferably about 16 hours.

The novel pharmaceutical formulations of this invention are adapted for oral administration such as tablets, capsules or the like; for nasal administration, especially in the form of a spray; for injection, in the form of a sterile injectable liquid; or for topical ocular administration in the form of solutions, ointments, solid water soluble polymeric inserts, or gels.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

5,6-dihydro-5-[3-(dimethylaminomethyl)-4-hydroxybenzyl]-4H-thieno[2,3-b]thiopyran-2-sulfonamide-7,7-dioxide Step A: Preparation of α-Methylene-4-methoxybenzenepropanoic acid 4-Methoxybenzylmalonic acid, (20.2 g., 0.09 mol) was suspended in N,N,$N^1$, $N^1$-tetramethylmethanediamine (45 ml). Acetic anhydride (45 ml) was added dropwise, keeping the temperature below 45° C. by cooling in an ice-bath as necessary. The resulting clear solution was stirred for 1½ hour at ambient temperature and then was poured into ice and water. The white solid product was collected, combined with comparable product from a second 0.083 mol run, and dried at 0.1 mm at room temperature to give 22.4 g. (68%) of product, m.p. 88°–91° C. A sample recrystallized from ether-petroleum ether melted at 90°–93° C.

Step B: Peparation of α-(4-Methoxybenzyl)-2-thiophenethioacetic acid

Under $N_2$, a mixture of α-methylene-4-methoxybenzenepropanoic acid (17.4 g, 0.09 mol), triethylamine (8.4 ml, 0.06 mol), 2-thiophenethiol (9.0 ml, 0.099 mol) and dry THF (120 ml) was stirred at reflux for 22 hours. Solvent was evaporated in vacuo and the residual oil, dissolved in $CHCl_3$, was washed with 3N HCl, the with $H_2O$ (3x), and dried over sodium sulfate. The solvent was evaporated under reduced pressure and the residue was triturated with hexane to yield 26.0 g, (94%) of the product as an off-white solid, m.p. 62°–66° C.

Step C: Preparation of 5,6-Dihydro-4H-5-(4-methoxybenzyl)-4-oxothieno[2,3-b]-thiopyran A solution of the product from Step B (25.9 g, 0.08 mol) in dry CH$_2$Cl$_2$ (85 ml) containing DMF (0.3 ml) was stirred at room temperature while oxalyl chloride (8.0 ml, 0.092 mol) was added dropwise. Stirring was continued for 2.5 hours. The mixture was cooled to −10° C. and a solution of SnCl$_4$ (4.9 ml, 0.042 mol) in dry CH$_2$Cl$_2$ (17 ml) was added dropwise at a rate such that the temperature was held below 5° C. After 1 hour at 0° C., H$_2$O (45 ml) was added dropwise, the temperature being held below 10° C. The layers were separated and the aqueous layer was extracted with CH$_2$Cl$_2$. The combined organic phases were washed with saturated NaHCO$_3$ solution, H$_2$O, saturated NaCl solution, and dried over Na$_2$SO$_4$. Evaporation of the solvent in vacuo left 24.3 g, (quantitative) of the product as a viscous, dark amber oil that slowly solidified on standing. An analytical sample was obtained by passage through a short column of silica gel, using 85 hexane:15 ethyl acetate as the eluant. Evaporation of the eluate gave a white crystalline solid, m.p. 91°–93° C.

Step D: Preparation of 5,6-Dihydro-4H-5-(4-methxoybenzyl)-4-oxothieno[2,3-b]thiopyran-2-sulfonamide To a stirred solution of the product from Step C (9.55 g, 0.033 mol) in dry CH$_2$Cl$_2$ (75 ml) was added acetic anhydride (10 g, 0.098 mol). The mixture was cooled to −10° C. and concentrated H$_2$SO$_4$ (3.3 g, 0.033 mol) was added dropwise at a rate such that the temperature remained below 0° C. After 2 hours at −10° C., a solution of potassium acetate (3.4 g, 0.034 mol) in 95% ethanol (20 ml) was added dropwise. The potassium sulfonate salt was precipitated by the addition of ether and the mixture was stirred at room temperature for 16 hours. The salt was collected and dried in vacuo at 50° C. for 4.5 hours; yield, 13.0 g (97%).

The potassium sulfonate salt (0.032 mol) was stirred in dry CH$_3$CN (250 ml) with PCl$_5$ (7.3 g, 0.035 mol) and 18-crown-6 (0.45 g) at room temperature for 64 hours. Solvent was stripped under reduced pressure and the residue was partitioned between CH$_2$Cl$_2$ and ice water. The organic phase was dried (MgSO$_4$) and concentrated to dryness. The residual oily sulfonyl chloride was dissolved in acetone (150 ml), cooled to 5° C., and treated with concentrated NH$_4$OH (75 ml). After 30 minutes, acetone was stripped in vacuo and the off-white solid product was collected from the aqueous residue, washed with water, and dried; 8.9 g (73%), m.p. 187°–190° C.

Step E: Preparation of 5,6-Dihydro-4H-5-(4-methoxybenzyl)thieno[2,3-b]thiopyran-2-sulfonamide A mixture of the product from Step D (7.4 g, 0.02 mol), triethylsilane (11.2 ml, 0.07 mol) and trifluoroacetic acid (30 ml) was stirred and heated to refluxing for 5 hours. The cooled mixture was neutralized with saturated NaHCO$_3$ solution and extracted with ethyl acetate (3x). The washed and dried ethyl acetate extract was concentrated in vacuo to obtain an oily solid residue that was suspended in ethanol (250 ml). Sodium borohydride (0.75 g, 0.02 mol) was added and the mixture was stirred at room temperature for 2 hours. During this period, all of the solid had dissolved. After cooling in an ice bath, the pH of the solution was adjusted to 8 with 1N HCl. Ethanol was stripped in vacuo and the residue was extracted into ethyl acetate. Evaporation of the washed and dried extract left a mixture of crude 5,6-dihydro-4H-5-(4-methoxybenzyl)thieno[2,3-b]thiopyran-2-sulfonamide and 5,6-dihydro-4H-4-hydroxy-5-(4-methoxybenzyl)-thieno[2,3-b]thiopyran-2-sulfonamide. The mixture was separated by chromatography on a silica gel 60 column, eluting with 97CHCl$_3$/3 CH$_3$OH/0.3H$_2$O. The fully reduced product came off the column first and was crystallized from CHCl$_3$ to obtain 1.8 g (36%), m.p. 152°–155° C. An analytical sample melted at 153°–155° C. after recrystallization from CHCl$_3$/CH$_3$OH. The recovery of the alcohol was 2.2 g, corresponding to 30% of the starting ketone.

Step F: Peparation of 5,6-Dihydro-4H-5-(4-hydroxybenzyl)thieno[2,3-b]thiopyran-2-sulfonamide 5,6-Dihydro-4H-5-(4-methoxybenzyl)thieno[2,3-b]thiopyran-2-sulfonamide (3.3 g, 9.3 mmol) was suspended in dry CH$_2$Cl$_2$ (150 ml), cooled in a dry ice-acetone bath, and treated with 1M BBr$_3$ in CH$_2$Cl$_2$ (27 ml). After 48 hours at room temperature, the mixture was quenched in ice, neutralized with saturated NaHCO$_3$ solution and extracted with ethyl acetate (3x). The combined organic phases were washed (saturated NaCl solution), dried (MgSO$_4$), and concentrated under reduced pressure. The residual crude product was chromatographed on a silica gel 60 column, eluting with 96CHCl$_3$/4CH$_3$OH/0.4H$_2$O to obtain 1.0 g (32%) of a dark yellow solid that was characterized by nmr.

Step G: Preparation of 5,6-Dihydro-4H-5-(4-hydroxybenzyl)thieno[2,3-b]thiopyran-2-sulfonamide-7,7-dioxide The product from Step F (1.0 g, 2.9 mmol) was dissolved in CH$_3$OH (30 ml) and a solution of OXONE (2.7 g, 4.4 mmol) in H$_2$O (25 ml) was added dropwise. The mixture was stirred at room temperature for 16 hours and then was filtered. After washing the filter cake thoroughly with CH$_3$OH, the filtrate was neutralized with saturated NaHCO$_3$ solution and concentrated under reduced pressure. The residual mixture was extracted with ethyl acetate. Evaporation of the washed and dried extract in vacuo gave 1.2 g of the product as a yellow glass. A sample was purified by Column chromatography on silica gel 60, eluting with 95CHCl$_3$/5CH$_3$OH/0.5H$_2$O. The solid product melted at 180°–186° C. dec.

Step H: 5,6-Dihydro-5-[3-(dimethylaminomethyl)-4-hydroxybenzyl]-4H-thieno[2,3-b]thiopyran-2-sulfonamide-7,7-dioxide hydrochloride The product from Step G (500 mg, 1.34 mmol), dimethylamine hydrochloride (300 mg, 3.68 mmol), 37% aqueous for aldehyde (0.13 ml) and glacial acetic acid (4 ml) were stirred and heated at 100° C. for 20 hours. The cooled mixture was neutralized with saturated NaHCO$_3$ solution and then was extracted repeatedly with ethyl acetate. Evaporation of the washed and dried extract left a mixture of the crude product and starting material as an off-white glass. This was combined with a comparable mixture from a second 1.34 mmole run and separated by chromatography on a silica gel column, eluting with 90CHCl$_3$/10CH$_3$OH/1H$_2$O. The product (300 mg.) came off the column last; 100 mg (10%) of the starting material was recovered. The product was purified further by conversion to the hydrochloride salt by treating a solution in ethanol with ethanolic HCl. Evaporation of the ethanol and trituration of the residue with n-propanol afforded 240 mg of the salt. This material was purified by chromatography on a silica gel column, eluting with 93CHCl$_3$/7CH$_3$OH/0.7 concentrated NH$_4$OH. The purified base was reconverted to the hydrochloride salt in ethanol by treatment with ethanolic HCl. Concentration of the solution in vacuo yielded 95 mg (7.6%) of desired product as a pale yellow glass after drying at 60° C. and 0.1 mm.

EXAMPLE 2

5,6-Dihydro-4H-4-hydroxy-6-(p-methoxyphenyl)-thieno[2,3-b]thiopyran-2-sulfonamide-7,7-dioxide

Step A: Preparation of 3-(p-Methoxyphenyl)-2-(2-mercaptothiophene)-propanoic acid A solution of 2-mercaptothiophene (6.5 g, 0.056 mol), THF (75 ml), p-methoxycinnamic acid (10 g, 0.056 mol), and C$_2$H$_5$)$_3$N (12.1 g, 0.12 mol) was heated at reflux under N$_2$. After 19 hours, another quantity of 2-mercaptothiophene (0.6 g, 0.0055 mol) was added to the reaction mixture. After an additional 5 hours at reflux, the reaction was poured into 3N HCl and the aqueous phase extracted with ethyl acetate (3x). The organic extracts were dried, filtered and concentrated to dryness. The residue was triturated with hexane and filtered to yield 15.7 g (95%) of product; m.p. 112°-114° C. (CH$_3$CN).

Step B: Preparation of 5,6-Dihydro-4H-6-(p-methoxyphenyl)thieno[2,3-b]thiopyran-4-one under N$_2$ in a 3-neck flask was placed product from Step A (70 g, 0.24 mol), DMF (1 ml) and CH$_2$Cl$_2$ (500 ml). To the stirred solution oxalyl chloride (33 g, 0.26 mol) was added dropwise at room temperature. After 1 hour, the solution was cooled to −10° C. and a solution of SnCl$_4$ (31.4 g, 0.12) in CH$_2$Cl$_2$ (14 ml) was added dropwise. The mixture was then stirred at 0° C. and after 0.5 hours, H$_2$O (250 ml) was added. The mixture was separated and the organic extract was washed with 5% NaOH solution, H$_2$O, dried, filtered and concentrated to dryness. The residue was chromatographed on silica gel (1L) and the product eluted with CH$_2$Cl$_2$ to yield 49.4 g (75%) of product; m.p. 82°-83° C. (CH$_2$Cl$_2$-ligroin).

Step C: Preparation of 5,6-Dihydro-4H-6-(p-methoxyphenyl)thieno[2,3-b]thiopyran-4-one-2-sulfonamide To an ice cooled solution of product from Step B (20.0 g, 0.072 mol) and acetic anhydride (21.2 g, 0.02 mol) in ethyl acetate (100 ml) there was added dropwise under N$_2$, concentrated H$_2$SO$_4$ (4.5 ml, 0.084 mol). After 1 hour, the solution was stirred at room temperature and a solution of potassium acetate (8.0 g, 0.082 mol) in 95% ethanol (40 ml) was added. After 2 hours, the solid was collected on a filter and dried in vacuo to yield 28 g of potassium salt.

To a suspension of the potassium salt (20 g, 0.05 mol) and 18-crown-6 (1 g) in CH$_3$CN (200 ml), PCl$_5$ (21 g, 0.1 mol) was added and the mixture heated at 60° C. with stirring. After 21 hours, the mixture was concentrated to dryness. The residue was partitioned between H$_2$O and CH$_2$Cl$_2$ (3x). The organic extract was dried, filtered and concentrated to dryness. The residue was dissolved in acetone and poured into concentrated NH$_4$OH. The solution was concentrated to dryness and the residue dry packed with silica gel. The dry pack was placed on a Still column (100 mm) and the product eluted with 3-5% CH$_3$OH—CH$_2$Cl$_2$ to yield 5.3 g (30%) of product; m.p. 228°-230° C. (CH$_3$CN).

Step D: Preparation of 5,6-Dihydro-4H-4-hydroxy-6-(p-methoxyphenyl)-thieno[2,3-b]thiopyran-2-sulfonamide To a suspension of the product from Step C (5.0 g, 0.014 mol) in absolute ethanol (75 ml) was added portionwise NaBH$_4$ (2.0 g, 0.05 mol). The mixture was heated at reflux with stirring. After 1 hour, the suspension was cooled, and the ethanol removed under reduced pressure (20 mm). Water was added to the residue and the pH adjusted to 8.5 with dilute acid (3N HCl). The suspension was extracted with ethyl acetate (3x) and the organic extract dried, filtered and concentrated to dryness. The residue was crystallized from CH$_3$OH—CH$_3$CN and filtered through a pad of filter aid and charcoal to yield 3.1 g (62%) of product; m.p. 215°-217° C.

Step E: Preparation of 5,6-Dihydro-4H-4-hydroxy-6-(p-methoxyphenyl)-thieno[2,3-b]thiopyran-2-sulfonamide-7,7-dioxide To a supension of product from Step D (2.45 g, 0.0069 mol) in CH$_3$OH (75 ml) stirred at room temperature was added dropwise a solution of "OXONE" (6.2 g, 0.01 mol) in H$_2$O (75 ml). After the addition, the mixture was heated at reflux for 1 hour, and stirred at room temperature for 1 hour. The CH$_3$OH was then removed under reduced pressure and the resulting aqueous layer extracted with ethyl acetate (4x). The organic extracts were dried, filtered and concentrated to dryness. The residue was recrystallized from CH$_3$CN to yield 1.8 g (67%) of product; m.p. 247°-248° C.

Employing the procedures substantially as described in Example 2, Steps A through E, but substituting for the 3-(4-methoxyphenyl)acrylic acid used in Step A, the 3-R$^3$-acrylic acids depicted in Table I, there are produced the 5,6-dihydro-4H-4-hydroxy-6-R$^3$-thieno[2,3-b]thiopyran-2-sulfonamide-7,7-dioxides also depicted in Table I by the following reaction scheme:

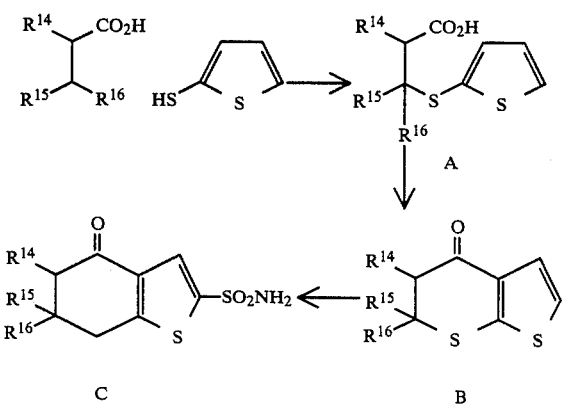

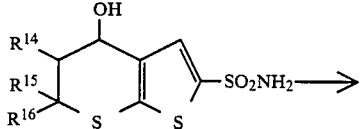

D

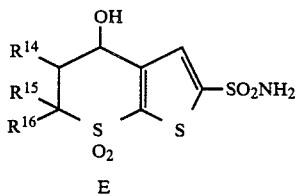

E

TABLE I

| | | | m.p. (°C.) of Product of Step | | | | |
|---|---|---|---|---|---|---|---|
| $R^{14}$ | $R^{15}$ | $R^{16}$ | A | B | C | D | E |
| H | furan-2-yl- | H | 81–83 | + | — | — | — |
| H | pyrid-2-yl- | H | — | — | — | — | — |
| H | pyrid-3-yl- | H | 98–100 | — | — | — | — |
| H | pyrid-4-yl- | H | 164–165 | — | — | — | — |
| H | thien-2-yl | H | 87.5–89 | + | — | — | — |
| H | 4-methoxybenzyl- | H | — | — | — | — | — |
| H | $CH_3-$ | $CH_3$ | 129* | 74.5–75 | 185.5–186.5 | 146–147 | 210–211 |
| H | $C_6H_5-$ | H | 61–63 | | | | |
| H | $4-NO_2-C_6H_4-$ | H | 152–154 | | | | |
| H | $2-NO_2-C_6H_4-$ | H | 81–3 | | | | |
| H | $C_2H_5-$ | $C_2H_5-$ | — | — | — | — | — |
| H | $C_2H_5-$ | $CH_3$ | — | — | — | — | — |
| H | $CH_3-$ | $m-C_3H_7$ | — | — | — | — | — |
| H | H | $CH_3-$ | 148** | + | + | + | 195–197 |
| H | H | $C_2H_5-$ | — | — | — | — | — |

+assigned structures supported by nmr.
*b.p. at 0.4 mm Hg.
**b.p. at 0.2 mm Hg.

EXAMPLE 3

5,6-Dihydro-4H-4-hydroxy-6-(p-hydroxyphenyl)-thieno[2,3-b]thiopyran-2-sulfonamide-7,7-dioxide

Step A: Preparation of 5,6-Dihydro-4H-6-(p-hydroxyphenyl)thieno[2,3-b]thiopyran-2-sulfonamide-4-one Under $N_2$, a suspension of 5,6-dihydro-4H-6-(p-methoxyphenyl)thieno[2,3-b]thiopyran-4-one (10.5 g, 0.03 mol) in $CH_2Cl_2$ (100 ml) was cooled to −78° C. while a solution of $BBr_3$ (1.0 m, 0.07 mol) in $CH_2Cl_2$ (70 ml) was added dropwise with stirring. The mixture was allowed to gradually warm to room temperature and then after overnight stirring poured onto ice. The aqueous phase was extracted with ethyl acetate (4x), and the organic layers were dried, filtered and concentrated to dryness. The residue was crystallized from $CH_3CN$ to yield 6.1 g of product. Chromtography of the mother liquor (4.6 g) on a Still column and elution with 5% $CH_3OH$—$CHCl_3$ gave an additional 1.5 g of product (68% total yield). $^1H$ NMR (DMSO) δ3.0 (m, 2H), 5.12 (dd, 1H), 6.78 (d, 2H) 7.37 (d, 2H), 7.73 (s, 1H), 7.81 (bs, 2H exch).

Step B: Preparation of 5,6-Dihydro-4H-4-hydroxy-6-p-hydroxyphenyl)-thieno[2,3-b]thiopyran-2-sulfonamide Under $N_2$, a mixture of product from Step A (1.5 g, 0.0044 mol) in absolute ethanol (25 ml) was stirred at room temperature while $NaBH_4$ (0.35 g, 0.0092 mol) was added portionwise. After the addition the mixture was heated at reflux for 1 hour and at room temperature for 1 hour. The suspension was then concentrated to dryness, $H_2O$ was added to the residue and the pH of the solution was adjusted to 8.5. The suspension was extracted with ethyl acetate (3x). The organic extracts were dried, filtered and concentrated to dryness to yield 1.3 g (97%) of product. $^1H$ NMR (DMSO) δ2.3 (m, 2H), 4.65 (m, 2H), 5.5 (br, 1H exch), 6.75 (d, 2H), 7.28 (d, 2H), 7.45 (s, 1H), 7.5 (s, 1H diasteriomer) 7.6 (bs, 2H exch)

Step C: Preparation of 5,6-Dihydro-4H-4-hydroxy-6-(p-hydroxyphenyl)-thieno[2,3-b]thiopyran-2-sulfonamide-7,7-dioxide Under $N_2$, a suspension of product from Step b, (1.3 g, 0.0038 mol) in $CH_3OH$ (50 ml) was stirred at room temperature while a solution of OXONE® (3.5 g, 0.0057 mol) in $H_2O$ (50 ml) was added dropwise. After overnight stirring, $H_2O$ was added and the mixture was extracted with ethyl acetate (3x). The organic extracts were dried, filtered and concentrated to dryness. The residue was dry packed on silica gel, placed on a Still column (50 mm) and the product eluted with 5% $CH_3OH$—$CHCl_3$ to yield 1.0 g (71%) of product; m.p. 263°–265° C. ($CH_3CN$—$CHCl_3$), $^1H$ NMR: (DMSO) δ2.38 (dd, 1H), 3.18 (m, 1H), 4.98 (dd, 2H), 6.05 (d, 1 H exch), 6.85 (d, 2H), 7.29 (d, 2H), 7.6 (s, 1H), 8.1 (bs, 2H exch). Other peaks were observed for the minor diasteriomer and by HPLC the mixture was 68.6%/31.4%.

EXAMPLE 4

5,6-Dihydro-4H-4-amino-6-(p-methoxyphenyl)-thieno[2,3-b]thiopyran-2-sulfonamide-7,7-dioxide hydrochloride

Step A: Preparation of 5,6-Dihydro-4H-4-acetamido6-(p-methoxyphenyl)-thieno[2,3-b]thiopyran-2-sulfonamide-7,7-dioxide To a solution of 5,6-dihydro-4H-4-hydroxy-6-(p-methoxyphenyl)thieno[2,3-b]thiopyran-2-sulfonamide-7,7-dioxide (9.3 g, 0.024 mol) in $CH_3CN$ (100 ml) cooled to 0°–4° C. was added dropwise under $N_2$ 96.6% $H_2SO_4$ (28 ml). After the addition, the reaction mixture was stirred at room temperature overnight. The dark brown solution was then poured onto ice and stirred for 1 hour. The resulting solid was filtered off to yield 2.9 g of product. The mother liquor was extracted with ethyl acetate (3x) and the organic extracts were washed with saturated NaHCO₃, dried, filtered and concentrated to dryness to yield 3.5 g of product (63% total yield); m.p. 279°–280° C. (CH₃CN).

Step B: Preparation of 5,6-Dihydro-4H-4-amino-6-(p-methoxyphenyl)-thieno[2,3-b]thiopyran-2-sulfonamide-7,7-dioxide hydrochloride A mixture of product from Step A (3.2 g, 0.0074 mol), 12N HCl (80 ml) and CH₃OH (80 ml) was heated at reflux for 19 hours. The mixture was then concentrated to dryness and the residue dry packed with silica gel and placed on a Still column (80 mm) and the product eluted with 10–12.5% CH₃OH—CHCl₃ to yield 1.6 g of product. The compound was prepared as the HCl salt from 4.65N HCl and crystallized from CH₃CN to yield 1.2 g (35.6%) of product; m.p. 225°–226° C.

Employing the procedures substantially as described in Example 4, Steps A and B, but using as starting materials, the 4-hydroxy compounds depicted in Table II, there are produced the 4-acetamido and 4-amino products also described in Table II, by the following reaction scheme:

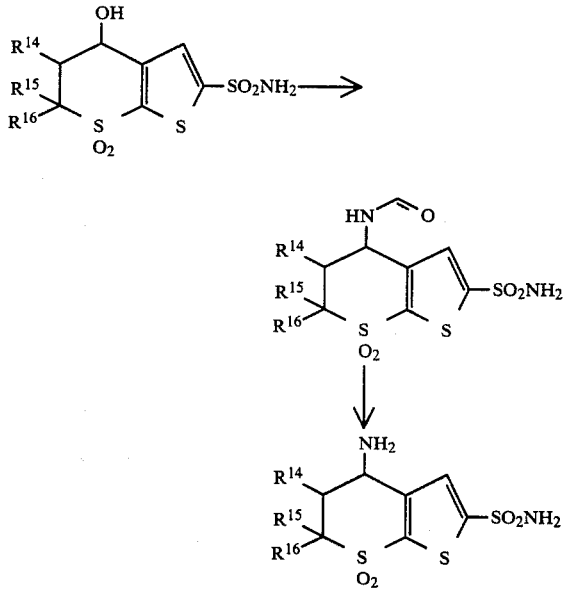

TABLE II

| R¹⁴ | R¹⁵ | R¹⁶ |
|---|---|---|
| 4-methoxybenzyl | H | H |
| H | furan-2-yl | H |
| H | pyrid-2-yl | H |
| H | pyrid-3-yl | H |
| H | pyrid-4-yl | H |
| H | thien-2-yl | H |
| H | 4-methoxybenzyl | H |

EXAMPLE 5

5,6-Dihydro-4H-4-ethylamino-6-(p-methoxyphenyl)-thieno[2,3-b]thiopyran-2-sulfonamide-7,7-dioxide hydrochloride Under N₂, a suspension of product from Example 4, Step A (4.0 g, 0.0093 mol) in THF (90 ml) was heated at reflux while a solution of borane dimethylsulfide complex (2.9 ml, 0.029 mol) was added dropwise with stirring. While heating at reflux, the generated dimethylsulfide was collected in a short path distillation apparatus. After 1.5 hour, the reaction mixture was allowed to stir to room temperature and then concentrated to dryness. The residue was treated with 12N HCl and heated at reflux for 0.5 hour. The suspension was then concentrated to dryness and dry packed with silica gel. The mixture was placed on a Still column (70 mm) and the compound eluted with CHCl₃:CH₃OH:aqueous concentrated NH₃ (90:10:1) to yield 2.5 g (51%) of product free base. The compound was treated with 4.65N HCl and crystallized from CH₃OH—C₂H₅OH to yield product; m.p. 235°–236° C.

Following the procedure substantially as described in Example 5, but using as starting materials the 4-acetamido compounds depicted in Table III, there are produced the 4-ethylamino compounds, also depicted in Table III by the following reaction scheme:

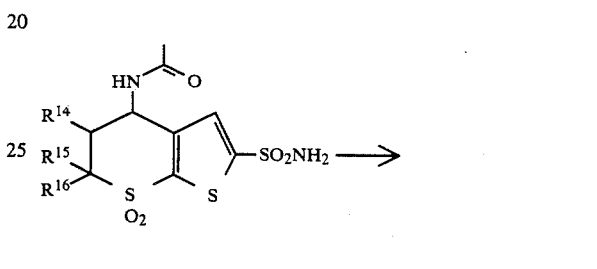

TABLE III

| R¹⁴ | R¹⁵ | R¹⁶ |
|---|---|---|
| 4-methoxybenzyl | H | H |
| H | furan-2-yl | H |
| H | pyrid-2-yl | H |
| H | pyrid-3-yl | H |
| H | pyrid-4-yl | H |
| H | thien-2-yl | H |
| H | 4-methoxybenzyl | H |

EXAMPLE 6

5,6-Dihydro-4H-4-isobutylamino-6-(p-methoxyphenyl)-thieno[2,3-b]thiopyran-2-sulfonamide-7,7-dioxide(α-isomer hydrochloride) and β-isomer hydrogen maleate)

Under N₂, a mixture of 5,6-dihydro-4H-4-hydroxy-6-(p-methoxyphenyl)thieno[2,3-b]thiopyran-2-sulfonamide-7,7-dioxide (4.9 g, 0.014 mol) in pyridine (20 ml) was cooled to −10° C. while p-toluene-sulfonyl chloride (5.3 g, 0.028 mol) was added portionwise. The resulting brown solution was stirred at −10° C. to 0° C. After 6 hours, isobutylamine (45 ml) was added at 0°–4° C. dropwise at a rate that the internal temperature did not exceed 15° C. After 2 hours, the temperature was raised to 50° C. and stirred overnight. The volatiles were removed first at reduced pressure (20 mm) and then high vacuum (1 mm). The residue was treated with 10% aqueous NaOH and ether and separated. The aqueous layer was adjusted to pH 8.5 and extracted with ethyl acetate (3x). The extracts were concentrated to dryness, the residue was dry packed with silica and placed on a Still column (100 mm). The mixture of diasteriomers was eluted from the column with 2-3% $CH_3OH$—$CHCl_3$ to yield 0.7 g of β-isomer, 1.8 g of α+β isomers and 1.3 g of α-isomer (61%). The α-isomer was treated with 4.5N HCl—$C_2H_5OH$ and crystallized from isopropanol-ethanol to yield product; m.p. 211°-214° C.

$^1$H NMR (DMSO) δ 1.0 (t, 6H), 2.12 (m, 1H), 2.65 (m, 1H), 2.0 (bd, 1H), 3.05 (bs, 1H), 3.19 (q, 1H), 3.82 (s, 3H), 5.05 (bs, 1H), 5.28 (d, 1H), 7.06 (d, 2H), 7.44 (d, 2H), 8.23 (bs, 2H exch), 8.28 (s, 1H).

Analysis: Calc'd for $C_{18}H_{24}N_2O_5S_3 \cdot HCl$. C, 44.94; H, 5.24; N, 5.82 Found: C, 45.15; H, 5.12; N, 5.80.

The β-isomer was crystallized as the maleate salt from $CH_3CN$ to yield product, m.p. 190°-192° C.

$^1$H NMR (DMSO) δ 0.94 (t, 6H), 1.88 (m, 1H), 2.65-3.5 (m, 4H), 3.81 (s, 3H), 4.65 (bs, 1H), 5.34 (d, 1H), 6.1 (s, 2H), 7.07 (d, 2H), 7.39 (d, 2H), 7.82 (bs, 1H), 8.19 (bs, 2H exch).

Analysis: Calc'd for $C_{18}H_{24}N_2O_5S_3 \cdot C_4H_4O_4$. C, 47.13; H, 5.03; N, 5.00 Found: C, 47.09; H, 5.05; N, 5.03.

Following the procedures substantially as described in Example 6, but using the 4-hydroxy-compounds and amines depicted in Table VI, there are produced the 4-substituted amino compounds also depicted in Table VI by the following reaction scheme:

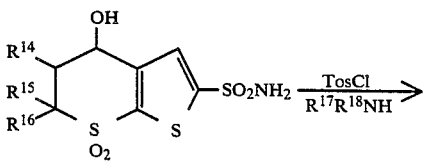

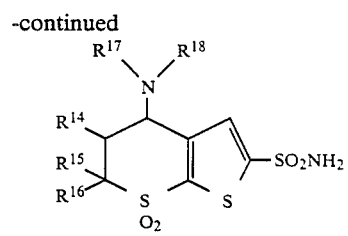

TABLE VI

| $R^{17}R^{18}N$— | $R^{14}$ | $R^{15}$ | $R^{16}$ |
|---|---|---|---|
| $(CH_3)_2CHCH_2NH$— | 4-methoxybenzyl | H | H |
| $(CH_3)_2CHCH_2NH$— | H | furan-2-yl | H |
| $(CH_3)_2CHCH_2NH$— | H | pyrid-2-yl | H |
| $(CH_3)_2CHCH_2NH$— | H | pyrid-3-yl | H |
| $(CH_3)_2CHCH_2NH$— | H | pyrid-4-yl | H |
| $(CH_3)_2CHCH_2NH$— | H | thieno-2-yl | H |
| $(CH_3)_2CHCH_2NH$— | H | 4-methoxybenzyl | H |
| $C_2H_5NH$— | H | furan-2-yl | H |
| $C_2H_5NH$— | H | pyrid-2-yl | H |
| $C_2H_5NH$— | H | pyrid-3-yl | H |
| $C_2H_5NH$— | H | pyrid-4-yl | H |
| $C_2H_5NH$— | H | the in-yl | H |
| $C_2H_5NH$— | H | 4-methoxybenzyl | H |
| $C_2H_5NH$— | 4-methoxybenzyl | H | H(m.p. 165-170° C.) |
| $n$-$C_3H_7NH$— | H | $CH_3$— | $CH_3$— |
| $C_2H_5NH$— | H | $C_2H_5$— | $C_2H_5$— |
| $(CH_3)_2CHCH_2NH$— | H | $C_2H_5$— | $CH_3$— |
| $C_2H_5NH$— | H | $CH_3$ | $n$-$C_3H_7$— |
| $C_2H_5NH$— (β-isomer) | H | H | $CH_3$—(m.p. 270-273° C. as HCl salt) |
| $C_2H_5NH$— (α-isomer) | H | H | $CH_3$—(m.p. 272-273° C. as HCl salt) |
| $(CH_3)_2CHCH_2NH$— (β-isomer) | H | H | $CH_3$—(m.p. 210-213° C. as HCl $0.5H_2O$) |
| $(CH_3)_2CHCH_2H$— (α-isomer) | H | H | $CH_3$—(m.p. 218° C. as maleate salt) |

EXAMPLE 7

5,6-Dihydro-4-ethylamino-6,6-dimethyl-4H-thieno[2,3-b]thiopyran-2-sulfonamide-7,7-dioxide Step A: Preparation of 5,6-Dihydro-4-ethylamino-6,6-dimethyl-4H-thieno[2,3-b]thiopyran-2-sulfonamide A solution of 5,6-dihydro-6,6-dimethyl-4H-thieno[2,3-b]thiopyran-4-one-2-sulfonamide (3.00 g, 0.011 mol) in dry tetrahydrofuran (40 ml) and benzene (40 ml) was cooled to −10° C. and condensed ethylamine (15 ml, 10.8 g, 0.24 mol) was added rapidly with stirring. Titanium tetrachloride 1.14 g, 0.006 mol) was added over 20 minutes while maintaining the temperature below 0° C. The mixture was stirred at ambient temperature for 2.5 hours, filtered, and the solid was washed with tetrahydrofuran. The combined filtrate and washings were evaporated in vacuo and the residue was suspended in absolute methanol (105 ml). With stirring under nitrogen, sodium borohydride (0.53 g, 0.014 mol) was added portionwise over 15 minutes and the mixture was stirred at ambient temperature for 21 hours. After acidification with concentrated hydrochloric acid, the mixture was concentrated in vacuo. The residue was distributed between water (100 ml) and ethyl acetate (100 ml), and the aqueous layer was separated and extracted with ethyl acetate (2×50 ml). The water layer then was basified with saturated sodium bicarbonate solution and extracted with ethyl acetate (3×250 ml). The combined extracts were washed with water (3x), dried over sodium sulfate, and evaporated in vacuo. The residue was crystallized as the hydrochloride salt from ethanolic hydrogen chloride to afford 2.60 g (69%) of pure product.

An analytical sample melted at 210°–211.5° C. after recrystallization from ethanol.

Anal. Calc'd for $C_{11}H_{18}N_2O_2S_3 \cdot HCl$: C, 38.53; H, 5.58; N, 8.17; Found: C, 38.49, H, 5.53; N, 8.03.

Step B: Preparation of 5,6-Dihydro-4-ethylamino-6,6-dimethyl-4H-thieno[2,3-b]thiopyran-2-sulfonamide-7,7-dioxide A solution of 5,6-dihydro-4-ethylamino-6,6-dimethyl-4H-thieno[2,3-b]thiopyran-2-sulfonamide (3.95 g, 0.013 mol) in methanol (85 ml) was acidified with 6.25N methanolic hydrogen chloride (2.1 ml). With stirring, a solution of 'OXONE' (11.68 g, 0.019 mol) in water (65 ml) was added over 15 minutes. After stirring at ambient temperature for 17.5 hours, the mixture was filtered and the solid was washed with methanol. The combined filtrate and washings were concentrated in vacuo below 55° C. to remove methanol and the cloudy aqueous solution was basified with saturated sodium bicarbonate solution. The mixture was extracted with ethyl acetate (150 ml and 2×100 ml), and the combined extracts were washed twice with water, dried over sodium sulfate and evaporated in vacuo. The amorphous residue was converted to the crystalline hydrochloride salt using ethanolic hydrogen chloride to yield 2.16 g (44%) of analytically pure product melting at 255°–255.5° C.

Anal. Calc'd for $C_{11}H_{18}N_2O_4S_3 \cdot HCl$: C, 35.24; H, 5.11; N, 7.47; Found: C, 35.31; H, 5.00; N, 7.53.

Employing the procedures substantially as described in Example 7, Steps A and B, but using as starting materials 6-($R^3R^4$)-4-oxo compounds and $R^5R^6NH$ depicted in Table VII there are produced the 6-$R^3R^4$-4-amino compounds also depicted in Table VII by the following reaction scheme:

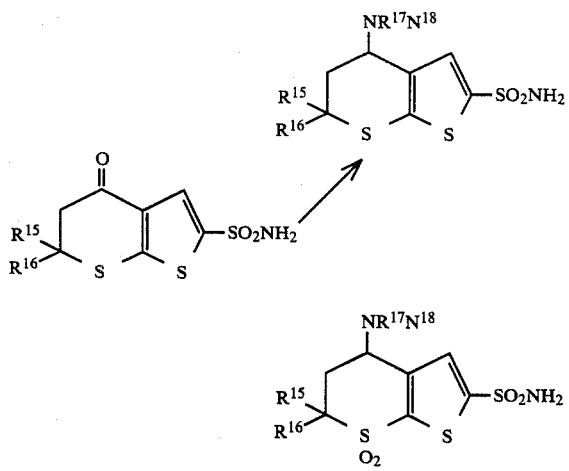

TABLE VII

| $R^{17}R^{18}N-$ | $R^{15}$ | $R^{16}$ |
|---|---|---|
| $(CH_3)_2CHCH_2NH-$ | $CH_3-$ | $CH_3-$ |
| $(CH_3)_2CHCH_2NH-$ | $C_2H_5-$ | $C_2H_5-$ |
| $(CH_3)_2CHCH_2NH-$ | $C_2H_5-$ | $CH_3-$ |
| $(CH_3)_2CHCH_2NH-$ | $CH_3-$ | $n-C_3H_7-$ |
| $C_2H_5NH-$ | $C_2H_5-$ | $C_2H_5-$ |
| $C_2H_5NH-$ | $C_2H_5-$ | $CH_3-$ |
| $C_2H_5NH-$ | $CH_3-$ | $n-C_3H_7-$ |

EXAMPLE 8

5-Cyano-5,6-dihydro-4H-4-hydroxythieno[2,3-b]thiopyran-2-sulfonamide

Step A: Preparation of $N^1$-(5,6-Dihydro-4-oxothieno[2,3-b]thiopyran-2-sulfonyl)-N,N-dimethylformamidine A stirred suspension of 5,6-dihydro-4-oxothieno[2,3-b]thiopyran-2-sulfonamide (13 g, 0.052 mol) in $CH_3CN$ (500 ml) was cooled in an ice bath and treated with N,N-dimethylformamide dimethyl acetal (7.6 ml, 0.057 mol). The ice bath was removed and stirring was continued at ambient temperature until all of the suspended solid had dissolved. Solvent was stripped under reduced pressure. The residual solid was recrystallized from ethylacetate decolorizing with charcoal, to obtain 12.8 g (82%) of product, m.p. 143°–145° C.

Step B: Preparation of $N^1$-(5-Diethoxymethyl-5,6-dihydro-4-oxothieno[2,3-b]thiopyran-2-sulfonyl)-N,N-dimethylformamidine Triethylorthoformate (43 ml, 0.25 mol) was stirred under $N_2$, and cooled to −30° C. while a solution of boron trifluoride etherate (35 ml, 0.284 mol) in $CH_2Cl_2$ (100 ml) was added dropwise. The resulting slurry of white solid was stirred without external cooling until the temperature was −10° C. and then it was cooled to −40° C. A solution of the product from Step A (31.2 g, 0.102 mol) in $CH_2Cl_2$ (100 ml) was added rapidly dropwise. N,N-Diisopropylethylamine (60 ml, 0.33 mol) then was added dropwise, keeping the temperature below −30° C. Stirring was continued at −30° C. for 30 minutes, then at −20° C. for 1½ hour. The mixture was quenched in saturated $NaHCO_3$ solution (1 L). After adding $CH_2Cl_2$ (400 ml), this mixture was stirred for 15 minutes at room temperature. The aqueous phase was separated and re-extracted with three portions of $CH_2Cl_2$. The combined organic phases were washed with ice-cold 2N $H_2SO_4$ (25 ml), then twice with ice water and dried over sodium sulfate. The solvent was evaporated under reduced pressure and the residue was triturated with cold $CH_3OH$ (50 ml) to yield 38.1 g (92%) of the product as an off-white solid, m.p. 92°–96° C.

Step C: Preparation of $N^1$-(5,6-Dihydro-5-hydroxymethylene-4-oxothieno[2,3-b]thiopyran-2-sulfonyl)-N,N-dimethylformamidine A stirred solution of the product from Step B (38 g, 0.0935 mol) in THF (300 ml) was treated with ice-cold 10% aq. HCl (200 ml). Stirring was continued for 48 hours. The separated yellow solid was collected, washed with ether, and dried to obtain 21 g of product, m.p. 206°–209° C. The filtrate was poured into saturated brine (500 ml) and this mixture was extracted with $CHCl_3$ (3×150 ml). Evaporation of the washed and dried extract under reduced pressure gave an additional 6.2 g of yellow solid product; combined yield, 88%.

Step D: Preparation of $N^1$-(5,6-Dihydro-4H-isoxazolo[4,5-d]thieno[2,3-b]thiopyran-2-sulfonyl)-N,N-dimethylformamidine A mixture of the product form Step C (27 g, 0.081 mol), hydroxylamine hydrochloride (8.4 g, 0.12 mol) and acetic acid (700 ml) was stirred and heated on a steam bath. After 40 minutes, the mixture was quenched in water (2 L.) After cooling in an ice bath, the solid product was collected, washed with water and dried to obtain 24.9 g (93%), m.p. 194°–196° C.

Step E: Preparation of 5,6-Dihydro-4H-isoxazolo[4,5-d]thieno[2,3-b]thiopyran-2-sulfonamide A mixture of the product from Step D (24.7 g, 0.075 mol), THF (550 ml) and 6N HCl (660 ml) was stirred at reflux for 4½ hours, then cooled in an ice bath and the solid product collected, washed with water, and dried; yield, 19.6 (96%); m.p. 212°–213° C.

Step F: Preparation of 5-cyano-5,6-dihydro-4-oxothieno[2,3-b]thiopyran-2-sulfonamide A solution of KOH (10 g, 0.18 mol) in $CH_3OH$ (475 ml) was stirred and cooled in an ice bath. The product from Step E (16.5 g, 0.06 mol) was added in portions and stirring was continued at 5°–10° C. for 2 hours. With continued cooling, the mixture was acidified by the dropwise addition of 95 ml 2N HCl. The solid product was collected, washed with water, and dried to yield 15.1 g (92%), m.p. dec. 198°–200° C.

Step G: Preparation of 5-Cyano-5,6-dihydro-4H-4-hydroxy-thieno[2,3-b]thiopyran-2-sulfonamide To a suspension of 5-cyano-5,6-dihydro-4-oxo-thieno[2,3-b]thiopyran-2-sulfonamide (5.5 g, 0.02 mol) in ethanol (400 ml) was added with stirring $NaBH_4$ (1.0 g). After 1 hour, the mixture was cooled in an ice bath and 0.1N HCl was added dropwise to pH 8. The ethanol was evaporated under reduced pressure. The product that crystallized from the aqueous residue was collected, washed with water and dried to obtain 4.0 g (72%), m.p. 177°–183° C.

An analytical sample was prepared by passage through a pad of silica gel, eluting with $CH_3OH/CHCl_3$ (1:1), followed by recrystallization from water; m.p. 183°–185° C.

EXAMPLE 9

5-Cyano-5,6-dihydro-4H-4-hydroxythieno[2,3-b]thiopyran-2-sulfonamide-7,7,-dioxide A solution of 5-cyano-5,6-dihydro-4H-4-hydroxy-thieno[2,3-b]thiopyran-2-sulfonamide (1.4 g, 0.005 mol) in $CH_3OH$ (25 ml) was stirred at room temperature while a solution of OXONE® (4.3 g, 0.0075 mol) in $H_2O$ (25 ml) was added dropwise. The mixture was stirred at room temperature for 3½ hours and then was filtered. Methanol was removed from the filtrated in vacuo and the aqueous residue was extracted with ethyl acetate (4x). The organic extracts were dried, filtered, and concentrated to dryness. The residue was crystallized from water to yield 1.2 g (78%) of product, m.p. 216°–219° C. (dec.). Recrystallization from $CH_3OH$–$CHCl_3$ gave material with m.p. 221°–223° C. (dec.).

EXAMPLE 10

5,6-Dihydro-4H-6-(p-methoxyphenyl)thieno[2,3-b]thiopyran-2-sulfonamide-7,7-dioxide

Step A: Preparation of 5,6-Dihydro-4H-6-(p-methoxyphenyl)thieno[2,3-b]thiopyran-2-sulfonamide Under $N_2$, triethylsilane (3.3 g, 28 mmol) was added dropwise to a solution of 5,6-dihydro-4H-4-oxo-6-(p-methoxyphenyl)thieno[2,3-b]thiopyran-2-sulfonamide (2.5 g, 7 mmol) in $CF_3CO_2H$ (12 ml, 17.8 g, 156 mmol). After the addition, the solution was heated at reflux with stirring for 2 hours and then at room temperature overnight. Saturated $NaHCO_3$ solution was added cautiously until the solution had pH 8.5, and the product was extracted with ethyl acetate (3x). The organic extracts were dried, filtered and concentrated to dryness. The residue was treated with $NaBH_4$ (1 g) in ethanol and the solution was heated at reflux. After 1 hour, the solution was poured into $H_2O$ and the solution was acidified with diluted HCl. The aqueous solution was extracted with ethyl acetate (3x). The organic extracts were washed with $NaHCO_3$, dried, filtered and concentrated to dryness. The residue (2.1 g) was dry packed with silica gel and chromatographed on a Still column eluting with 2.5% $CH_3OH$—$CHCl_3$ to yield 0.9 g (37%) of product.

Step B: Preparation of 5,6-Dihydro-4H-6-(p-methoxyphenyl)-thieno[2,3-b]thiopyran-2-sulfonamide-7,7-dioxide A suspension of product from Step A (0.9 g, 0.0026 mol), $CH_3OH$ (15 ml) $H_2O$ (30 ml), and "OXONE" (2.3 g, 0.0038 mol) was stirred at room temperature overnight. The mixture was poured into $H_2O$ and extracted with ethyl acetate (7x). The organic extracts were dried, filtered and concentrated to dryness. The residue was then treated with $CH_3OH$ (30 ml), $H_2O$ (30 ml) and "OXONE" (2.3 g, 0.0038 mol) and the mixture heated at reflux with stirring. After 1 hour, the mixture was cooled to room temperature, poured into $H_2O$ and extracted with ethyl acetate (3x). The organic extracts were dried, filtered and concentrated to dryness to yield 0.8 g (80%) of product; m.p. 244°–246° C. ($CH_3OH$–$CH_3CN$).

EXAMPLE 11

5,6-Dihydro-4H-6-(4-hydroxy-3-dimethylaminomethylphenyl)thieno[2,3-b]thiopyran-2-sulfonamide-7,7-dioxide

Step A: Preparation of 5,6-Dihydro-4H-6-(p-hydroxyphenyl)thieno[2,3-b]thiopyran-2-sulfonamide-7,7-dioxide To a mixture of 5,6-dihydro-4H-4-hydroxy-6-(p-hydroxyphenyl)thieno[2,3-b]thiopyran-7,7-dioxide (6.4 g, 0.0017 mol), $CH_3CN$ (90 ml), and NaI (22 g, 0.146 mol) was added with stirring under $N_2$ dimethyldichlorosilane (8.2 ml, 8.7 g, 0.068 mol). After the addition, the mixture was heated at reflux for 2 hours and then poured into $H_2O$. The aqueous phase was extracted with ethyl acetate (3x). The organic extracts were washed with saturated $NaHCO_3$ and 10% $Na_2SO_3$, dried, filtered and concentrated to dryness. The residue was triturated with $CHCl_3$ to yield 3.4 g of product. The mother liquor was chromatographed on a Still column and the product eluted with 5% $CH_3OH$—$CHCl_3$ to yield an additional 1.0 g of product (72% total yield). An analytical sample was prepared by crystallization from $CH_3OH$—$CHCl_3$. m.p. 268°–269° C.

Step B: Preparation of 5,6-Dihydro-4H-6-(4-hydroxy-3-dimethylaminomethylphenyl)thieno[2,3-b]thiopyran-2-sulfonamide-7,7-dioxide hydrochloride A solution of product from Step A (1.2 g, 3,3 mmol), dimethylamine hydrochloride (1.2, 14.7 mmol), acetic acid (15 ml), and 37% formaldehyde (0.6 ml, 7.4 L mmol) was heated at 100° C. with stirring under N$_2$. After 18 hours, the solution was concentrated to dryness and the residue partitioned between saturated NaHCO$_3$ and ethyl acetate. The aqueous phase was further extracted with ethyl acetate (3x) and the organic extracts dried, filtered and concentrated to dryness. The residue was dry packed on silica gel and chromatographed on a Still column. The product was eluted with 75% CH$_3$OH—CHCl$_3$ to yield 0.3 g of product (22%). The product was treated with ethanolic HCl and crystallized from CH$_3$OH-isopropanol to yield the product. m.p. 298°-300° C.

EXAMPLE 12

5,6-Dihydro-4H-4-(4-methoxyphenyl)thieno[2,3-b]thiopyran-7,7-dioxide

Step A: Preparation of 2-(3-hydroxy-3-p-methoxyphenylpropyl)thiothiophene

To a suspension of magnesium turnings (1.7 g, 0.07 mol) in THF (20 ml) was added dropwise a solution of 1-bromo-4-methoxybenzene (5.2 ml, 0.041 mol) and 1,2-dibromoethane (1.8 ml, 0.021 mol) in THF (40 ml). The reaction mixture was cooled to −10° C. and a solution of 3-(2-thienylthio)propionaldehyde in THF (30 ml) was added dropwise. After addition, the reaction was stirred at −10° C. for 1 hour and then at room temperature overnight. Saturated NH$_4$Cl solution was added dropwise, the mixture filtered through filter-aid and the solid washed with CHCl$_3$. The filtrate was concentrated, water added and extracted with CHCl$_3$. Drying and solvent evaporation gave an oil (5.9 g); column chromatography (silica gel, 10% ethyl acetate-hexane) gave the product (2.9 g, 60%).

Step B: Preparation of 5-(3-hydroxy-3-p-methoxyphenylpropyl)thiothiophene-2-sulfonamide To a solution of product from Step A (3.3 g, 0.012 mol) in THF (60 ml), cooled to −23° C. was added n-butyllithium (15.0 ml, 1.6M in ether-hexane, 0.024 mol) dropwise. The mixture was stirred at −23° C. for 2 hours. The reaction was cooled to −78° C. and liquid SO$_2$ (0.5 ml, 0.012 mol) was added. After stirring at room temperature for 1.5 hours, acetic acid (0.7 ml) and hexane (60 ml) were added, the reaction mixture was filtered and the solid washed with hexane. The solid was dissolved in water (20 ml) and sodium acetate (1.6 g, 0.012 mol) and hydroxylamine-O-sulfonic acid (1.6 g, 0.014 mol) were added. The mixture was then stirred at room temperature overnight. The aqueous phase was then extracted with ethyl acetate and the combined organic layers were dried. Solvent evaporation gave an oil (2.4 g). Column chromatography (silica gel, 40% ethyl acetate-hexane) and recrystallization frm CHCl$_3$ gave product (1.2 g, 28%); m.p. 111°-112° C.

Step C: Preparation of 5,6-Dihydro-4H-4-(p-methoxyphenylthieno[2,3-b]thiopyran-2-sulfonamide A solution of sulfuric acid (9.3 ml) in water (9.3 ml) was cooled to 0° C. A solution of product from Step B (0.5 g, 1.4 mmol) in THF (9.3 ml) was added dropwise and the reaction was stirred at room temperature for 1 hour. The mixture was concentrated, water added, extracted with ethyl acetate and the organic layers were washed with saturated bicarbonate solution and water. Drying and solvent evaporation gave product (0.5 g).

Step D: Preparation of 5,6-Dihydro-4H-4-p-methoxyphenylthieno[2,3-b]thiopyran-2-sulfonamide-7,7-dioxide To a solution of product from Step C (1.9 g, 5.6 mmol) in methanol (33 ml) was added a solution of OXONE (5.8 g, 9.5 mmol) in water (33 ml) dropwise and the resulting suspension was stirred at room temperature overnight. The mixture was concentrated, water added and extracted with ethyl acetate. Drying and solvent evaporation gave an oil (2.2 g). Column chromatography (silica gel, 50% ethyl acetate-hexane) gave product (1.7 g, 81%); m.p. 200°-202° C.

EXAMPLE 13

5,6-Dihydro-4H-p-hydroxyphenylthieno[2,3-b]thiopyran-b 2-sulfonamide-7,7-dioxide To a suspension of product from Example 12 (1.3 g, 3.5 mmol) in CH$_2$Cl$_2$ (58 ml), cooled to −78° C., was added boron tribromide (11.2 ml, 1.0M in CH$_2$Cl$_2$, 11.2 mmol) dropwise and the resulting mixture was stirred at room temperature for 3 hours. The reaction was cooled to 0° C., water and saturated bicarbonate solution added and extracted with ethyl acetate. Drying and solvent evaporation gave a solid (1.6 g). Recrystallization from CHCl$_3$ gave the product (1.0 g, 83%); m.p. 219°-222° C.

EXAMPLE 14

5,6-Dihydro-4H-4-(4-hydroxy-3-dimethylaminomethylphenyl)thieno[2,3-b]thiopyran-2-sulfonamide-7,7-dioxide To a solution of product from Example 13 (2.0 g, 5.6 mmol) in ethanol (28 ml) were added formaldehyde (0.5 ml, 37% in water, 6.2 mmol) and dimethylamine (1.4 ml, 40% in water, 11.2 mmol). The reaction was refluxed for 3 hours and then stirred at room temperature overnight. The solution was concentrated, 3N HCl added and extracted with ethyl acetate. The aqueous phase was made basic with saturated bicarbonate solution and extracted with ethyl acetate. Drying and solvent evaporation gave an oil (1.0 g) column chromatography (silica gel, 5% methanol-CHCl$_3$) gave product (1.0 g, 43%); m.p. 182°-185° C.

EXAMPLE 15

6,7-Dihydro-5H-7-hydroxy-5-methylthieno[3,2-b]thiopyran-2-sulfonamide-4,4-dioxide Step A: Preparation of 3-(3-mercaptothiophene)-3-methylpropionic acid A mixture of crotonic acid (2.7 g., 0.28 mol), THF (40 ml), (C$_2$H$_5$)$_3$N (1.45 g, 0.14 mol) and 3-mercaptothiophene (3.6 g, 0.03 mol) was heated at reflux under N$_2$. After 21 hours, the solution was poured into dilute aqueous HCl and extracted with ethyl acetate (3x). The organic extracts were dried, filtered and concentrated to dryness to yield the title compound in 93% yield.

Step B: Preparation of 6,7-Dihydro-5H-7-oxothieno[3,2-b]thiopyran

Under N$_2$ in a three-necked flask was placed product from Step A (59.3 g, 0.29 mol), DMF (1.5 ml) and CH$_2$Cl$_2$ (450 ml). To the stirred solution was added dropwise at ambient temperature oxalyl chloride (40.7 g, 0.32 mol). After 1 hour, the solution was cooled to −10° C. and a solution of SnCl$_4$ (40 g, 0.15 mol) in CH$_2$Cl$_2$ (100 ml) was added dropwise. The mixture was stirred at 0° C. and after 0.5 hour H₂O (300 ml) was added. The mixture was separated and the organic extract is washed with saturated Na₂CO₃, H₂O, and brine, dried, filtered and concentrated to dryness to yield the title compound in quantitative yield.

Step C: Preparation of
6,7-Dihydro-5H-7-hydroxy-5-methylthieno[3,2-b]thiopyran

Under N₂, a mixture of product from Step B (11 g, 0.06 mol), ethanol (75 ml) and NaBH₄ (2.5 g, 0.065 mol) was stirred at room temperature. After 0.5 hour, the mixture was heated at reflux for 1 hour, cooled and then concentrated to dryness. The residue was partitioned between H₂O and CHCl₃ (3x) and the organic extracts were dried, filtered and concentrated to dryness to yield the title compound in 87% yield.

Analysis calc'd for $C_8H_{10}OS_2$: C, 61.63; H, 5.41. Found: C, 51.37; H, 5.54.

Step D: Preparation of
6,7-Dihydro-5H-7-(methoxyethoxymethoxy)-5-methylthieno[3,2-b]thiopyran To a solution of product from Step C (26 g, 0.14 mol) under N₂, diisopropylethylamine (28.2 g, 0.21 mol) and CH₂Cl₂ (300 ml) was added dropwise a solution of methoxyethoxymethylchloride (25 ml, 0.22 mol) and the solution was stirred at room temperature. After 72 hours, the reaction was washed with 1N HCl, saturated NaHCO₃ solution and H₂O. The organic layer was dried, filtered and concentrated to dryness. The residue was chromatographed on a Still column (100 mm) and the product eluted with 20% ethylacetate-hexane to provide the title compound in 18% yield.

Step E: Preparation of
6,7-Dihydro-5H-7-(methoxyethoxymethoxy)-5-methylthieno[3,2-b]thiopyran-2-sulfonamide Under N₂, a solution of product from Step D (39.7 g, 0.145 mol) in THF (500 ml), was cooled to −78° C. and a solution of n-BuLi (1.6M, 100 ml, 0.16 mol) was added dropwise. After 0.5 hour, SO₂ gas was passed over the surface for 40 minutes. After the addition, the mixture was stirred for 2 hours at room temperature. The mixture was then treated with H₂O (560 ml), sodium acetate 3H₂O (45 g, 0.54 mol) and hydroxylamine-o-sulfonic acid (30.5 g, 0.27 mol). After stirring overnight at room temperature, the aqueous suspension was extracted with ethyl acetate (3x). The organic extracts were dried, filtered and concentrated to dryness. The residue was chromatographed on a Still column (100 mm) and the product was eluted with 4% CH₃OH-CHCl₃ to yield the title compound in 21% yield.

Step F: Preparation of
6,7-Dihydro-5H-7-(methoxyethoxymethoxy)-5-methylthieno[3,2-b]thiopyran-2-sulfonamide-4,4-dioxide To a solution of oxone (10.4 g, 0.017 mol) in H₂O (100 ml) is added dropwise a solution of product from Step F (4.0 g, 0.011 mol) in CH₃OH (100 ml). After stirring at room temperature overnight, the mixture was cooled to −10° C. and sulfuric acid (100 ml) was added. After a 0.5 hour in the cold and 1 hour at room temperature, the mixture was added to H₂O and extracted with ethyl acetate (5x). The organic extracts were dried, filtered and concentrated to dryness. The residue was chromatographed on a Still column (40 mm) and the product eluted with 5% CH₃OH-CHCl₃ to provide the title compound in 19% yield; m.p. 219°–221° C.

Analysis Calc'd for $C_8H_{11}NO_5S_3$: C, 32.34; H, 3.73; N, 4.71. Found: C, 32.26; H, 3.67; N, 4.72.

EXAMPLE 16

6,7-Dihydro-5H-7-(ethylamino)-5-methylthieno[3,2-b]thiopyran-2-sulfonamide-4,4-dioxide (9)

Step A: Preparation of
6,7-Dihydro-5H-7-acetamido-5-methylthieno[3,2-b]thiopyran-2-sulfonamide-4,4-dioxide To a cooled solution (0.7° C.) of product from Example 15 Step G (3.6 g, 0.012 mol) in CH₃CN (75 ml) is added dropwise concentrated H₂SO₄ (12.3 ml). After addition, the mixture is stirred at room temperature overnight and then poured onto ice (300 g). After stirring for 1 hour, the mixture is extracted with ethyl acetate (3x). The organic extracts are dried, filtered and concentrated to yield the title compound.

Step B: Preparation of
6,7-Dihydro-5H-7-(ethylamino)-5-methylthieno[3,2-b]thiopyran-2-sulfonamide-4,4-dioxide Into a 2-necked flask fitted with a short path distillation head is added product from Step A (2.5 g, 0.0075 mol) and THF (40 ml). The mixture is heated at gentle reflux and a solution of BH₃.(CH₃)₂S (2.4 ml of 10M, 24 mmol) is added very carefully. The mixture is heated at reflux for 0.5 hour and then treated with 6N HCl (20 ml). The mixture is concentrated to dryness to yield the title compound as the hydrochloride salt.

EXAMPLE 17

6,7-Dihydro-5H-7-amino-5-methylthieno[3,2-b]thiopyran-2-sulfonamide-7,7-dioxide

A mixture of product from Example 16 (5.2 g, 0.015 mol), CH₃OH (50 ml) and 12N HCl (50 ml) is heated at reflux. After 6 hours, the mixture is concentrated to dryness to yield the title compound as the hydrochloride salt.

EXAMPLE 18

6,7-Dihydro-5H-7-isobutylamino-5-methylthieno[3,2-b]thiopyran-2-sulfonamide 4,4-dioxide A mixture of product from Example 17 (3.3 g, 0.01 mol), THF (100 ml), and Et₃N (3 ml) is stirred at room temperature while a solution of isobutyryl chloride (1.1 g, 0.01 mol) in THF (10 ml) is added dropwise. The mixture is stirred at room temperature overnight and then treated with saturated NaHCO₃ solution. The mixture is extracted with ethyl acetate (3x). The organic extracts are dried, filtered, and concentrated to dryness to yield the amide. Reduction of the amide as described in Example 16, Step B provides the title compound.

EXAMPLE 19

6,7-Dihydro-5H-7-hydroxy-5-methylfurano[3,2-b]thiopyran-2-sulfonamide-4,4-dioxide Step A: Preparation of 3-(3-Furylthio)crotonic acid A solution of 3-bromofuran (2.00 g, 0.014 mole) in ether (5 ml) is added over 15 minutes to a stirred solution of 1.6M n-butyllithium in hexane (10 ml, 0.016 mole) at −70° C. under a nitrogen atmosphere. The mixture is stirred for an additional 10 minutes and then sulfur (0.51 g, 0.016 mole) is added portionwise over 5 minutes. The mixture is stirred at −70° C. for 30 minutes, then allowed to warm to −15° C. The solution is then poured into H₂O, separated, and the aqueous layer extracted with ether (1X), and added to a solution of crotonic acid (1.28 g, 0.014 mol) and K₂CO₃ (1.9 g, 0.014 mol) in H₂O. The reaction mixture is allowed to stir at room temperature overnight. The aqueous layer is extracted with ether (1X), acidified with 6NHCl, and then extracted with ether (4X). The organic extracts are dried, filtered and concentrated to dryness to yield the product.

Step B: Preparation of
6,7-Dihydro-5H-5-methylfurano[3,2-b]thiopyran-7-one

A mixture of 3-(3-furylthio)crotonic acid (4.3 g, 0.025 mol), SUPER CEL ® (5 g), and P₂O₅ (8 g) in toluene (80 ml) is mechanically stirred under N₂ at 100° C. After 2 hours, additional P₂O₅ (8 g) is added and the mixture heated for 3 hours at 100° C. The mixture is filtered, and the solid is washed with hot toluene (3X), and the filtrate concentrated to dryness to yield the product.

Step C:
6,7-Dihydro-5H-7-hydroxy-5-methylfurano[3,2-b]thiopyran-2-sulfonamide-4,4-dioxide The procedure utilized to prepare 6,7-dihydro-5H-7-hydroxy-5-methylthieno[3,2-b]thiopyran-2-sulfonamide-4,4-dioxide (Example 15, Steps C, D, E, and F) is used to prepare the product.

EXAMPLE 20

Employing procedures substantially as described in the Examples cited below but starting with an N-(C₁₋₃alkyl)pyrrole or an N-benzyl pyrrole analog of the thiophene starting materials used in the cited examples there are prepared the corresponding pyrrolo[3,2-b]thiopyrans as follows:
Example 15 Steps B, C, D, E and F
  6,7-dihydro-5H-hydroxy-1,5-dimethylpyrrolo[3,2-b]thiopyran-2-sulfonamide-4,4-dioxide; and
  6,7-dihydro-5H-7-hydroxy-5-methylpyrrolo[3,2-b]thiopyran-2-sulfonamide-4,4-dioxide;

EXAMPLE 21

5,6-Dihydro-6-dimethylaminomethyl-4H-thieno[2,3-b]thiopyran-2-sulfonamide

Step A: Preparation of 2-(2-thienylthio)succinic acid

To a stirred solution of maleic acid (6.38 g, 0.055 mol) in tetrahydrofuran (50 ml) under nitrogen atmosphere was added 2-thiophenethiol (5.0 ml, 0.055 mol) and triethylamine (14.2 g, 0.14 mol). The mixture was stirred at gentle reflux for 16 hours overnight. The solvent was removed in vacuo and the residual oil was poured into 3NHCl (200 ml). The product was extracted into ethyl acetate (125 ml) in three portions, washed with saturated NaCl solution and dried over Na₂SO₄. The solution was filtered and concentrated in vacuo. This procedure gave the product as a light beige solid, 11.9 g, m.p. 136°–138.5° C. of 95% purity by HPLC. Yield was 93%.

Step B: Preparation of
5,6-dihydro-4-oxo-4H-thieno[2,3-b]thiophene-6-carboxylic acid To a stirred suspension of 2-(2-thienylthio)succinic acid (75.5 g, 0.325 mol) in methylene chloride (500 ml) under a nitrogen atmosphere was added dimethylformamide (3 ml) followed by the dropwise addition of oxalyl chloride (70.7 ml, 0.81 mol) over a ½ hour period. The mixture was stirred at ambient temperature for 2½ hours and the resulting solution was concentrated in vacuo to a brown oil. Then ½ of this oil was dissolved in methylene chloride (200 ml), cooled to about −78° C. and stirred as trifluoromethane sulfonic acid (50 g, 0.33 mol) was added dropwise over 5 minutes. After ¼ hour at −78° C., the cooling bath was removed and the temperature was allowed to rise to room temperature. After 4¾ hours, the mixture was poured into ice and water. Methylene chloride (400 ml) was added and the mixture was filtered to obtain the product as a pale gray solid (4.1 g). The methylene chloride layer was separated, washed with H₂O, dried over Na₂SO₄, filtered and concentrated in vacuo to a black gum. The gum was dissolved in ethyl acetate (150 ml). This solution was extracted with 10×50 ml of 0.25N KOH. The individual extracts were acidified and solids were filtered and dried. Total product obtained was 19 g or 55% yield. Pure product melted at 182.5°–184° C.

Step C: Preparation of
N,N-dimethyl-4-oxo-4H-thieno[2,3-b]thiopyran-6-carboxamide Under a nitrogen atmosphere, to a stirred solution of 4-oxo-4H-thieno[2,3-b]thiopyran-6-carboxylic acid (10.7 g, 0.05 mol) in tetrahydrofuran (50 ml) was added carbonyldiimidazole (8.9 g, 0.055 mol). The mixture was stirred at ambient temperature for ¾ hour. Anhydrous dimethylamine was bubbled into the thick suspension at 0° C. until an excess was present. The resulting solution was stirred at 0° C. for ¾ hour and the solvent was removed in vacuo. The residual oil was diluted with H₂O (50 ml) and the solid which separated was filtered and dried to give 7.14 g of product, m.p. 126.5°–128 of 97% purity by HPLC. The aqueous filtrate was concentrated in vacuo and the residual gum was chromatographed on silica gel (200 g) using 10% methanol in chloroform. An additional 3.15 g of impure product was recovered. Yield was about 80%.

Step D: Preparation of
5,6-dihydro-6-dimethylaminomethyl-4H-thieno[2,3-b]thiopyran To a stirred, refluxing solution of N,N-dimethyl-4-oxo-5,6-dihydro-4H-thieno[2,3-b]thiopyran-6-carboxamide (7.57 g, 0.0314 mol) under nitrogen in tetrahydrofuran (150 ml) was added dropwise over 10 minutes borane-dimethylsulfide complex (9.4 ml, 0.094 mol). Stirring at reflux was continued for 3 hours and 6NHCl (25 ml) was added dropwise and reflux was continued for ½ hour. Most of the tetrahydrofuran was removed in vacuo and the residue was diluted with 6NHCl (50 ml) and was heated for ½ hour at steam bath temperature under nitrogen. The mixture was cooled in ice and water (100 ml) was added to dissolve the solid, washed with ether (50 ml) and basified with 10H NaOH (75 ml). The product was extracted into ethyl acetate (200 ml) in four portions, washed with water and dried over Na₂SO₄. The solution was filtered and concentrated in vacuo to obtain an amber oil (5.7 g). Yield was 85%.

Step E: Preparation of
5,6-dihydro-6-dimethylaminomethyl-4H-thieno[2,3-b]thiopyran-2-sulfonamide n-Butyllithium (9.4 ml, 0.015 mol of a 1.6M solution in hexane) was added dropwise over 15 minutes at −78°

C. under nitrogen to a stirred solution of 5,6-dihydro-6-dimethylaminomethyl-4H-thieno[2,3-b]thipyran in tetrahydrofuran (25 ml). After ½ hour at −78° C., anhydrous SO₂ was bubbled over the surface of the solution until the mixture was essentially neutral. Then the addition of SO₂ was stopped and the yellow solution was stirred at −78° C. for 1 hour. The solvent and excess SO₂ were removed in vacuo and a light tan foam remained. This residue was taken up in 50 ml of water containing sodium acetate (1.8 g, 0.022 mol) and hydroxylamine-o-sulfonic acid (2.26 g, 0.02 mol) was added. The neutral solution was stirred at room temperature over night. Excess NaHCO₃ was added and the mixture was extracted with ethyl acetate (3×25 ml). The combined ethyl acetate solutions were extracted with 1M KOH (2×25 ml), washed with ether, acidified with excess 6NHCl and again extracted with ethyl acetate (2×50 ml) and with chloroform (50 ml). The combined extracts were washed with water, dried over Na₂SO₄, filtered and concentrated in vacuo to obtain 0.77 g of pale yellow solid, m.p. 148°–152° C. Re-extraction of the ether wash and ethyl acetate solutions with HCl followed by NaHCO₃ basification and chloroform extraction gave an additional 2.1 g of crude product which yielded 1.84 g of pure product upon chromatography on silica gel (50 g) using 10% methanol in chloroform. Yield was 60%.

A sample was converted to the hydrochloride salt, m.p. 229°–230° C.

Employing the procedure substantially as described in Example 21 but substituting for the maleic acid in Step A, a dicarboxylic acid of structure HOOCCH=CH(CH₂)$_p$COOH and employing an amine of structure R$^{17}$R$^{18}$NH in Step C, there are produced 6-aminoalkyl-compounds described in Table VIII in accordance with the following reaction scheme:

TABLE VIII-continued

| P | R$^{17}$ | R$^{18}$ |
|---|---|---|
| 2 | —CH₂CH₃ | H |
| 2 | —CH(CH₃)₂ | —CH₃ |
| 3 | —CH₂CH(CH₃)₂ | H |
| 4 | —CH₂CH(CH₃)₂ | —CH₃ |
| 2 | —CH₂CH₂—O—CH₂CH₂— | |
| 2 | —CH₂CH₂—CH₂—CH₂CH₂— | |
| 2 | —CH₂CH₂—CH₂CH₂— | |
| 2 | —CH₂CH₂—N—CH₂—CH₂<br>           \|<br>          CH₃ | |
| 2 | —CH₂—⟨△⟩ | H |

EXAMPLE 22

5,6-Dihydro-6-dimethylaminomethyl-4H-thieno[2,3-b]thiopyran-2-sulfonamide-7,7-dioxide and 5,6-dihydro-6-methylene-4H-thieno[2,3-b]thiopyran-2-sulfonamide-7,7-dioxide 5,6-Dihydro-6-dimethylaminomethyl-4H-thieno[2,3-b]thiopyran-2-sulfonamide (1.46 g, 0.005 mol) was dissolved in 10 ml of ethanol and 5 ml of water with warming and Oxone® (4.6 g, 0.0075 mol) was added and stirring was continued at room temperature for 5 hours. The mixture was neutralized by carefully adding solid NaHCO₃. An additional 10 ml of water and 25 ml of ethyl acetate were added and the mixture was filtered. The filtrate was dried over Na₂SO₄, filtered and concentrated in vacuo to give 0.68 g of light amber gum. The solids from the filtration were stirred in 50 ml of methanol and the mixture was filtered. This gave 0.65 g of white solid. Both of these products were mixtures of the same two major components. The gum was chro-

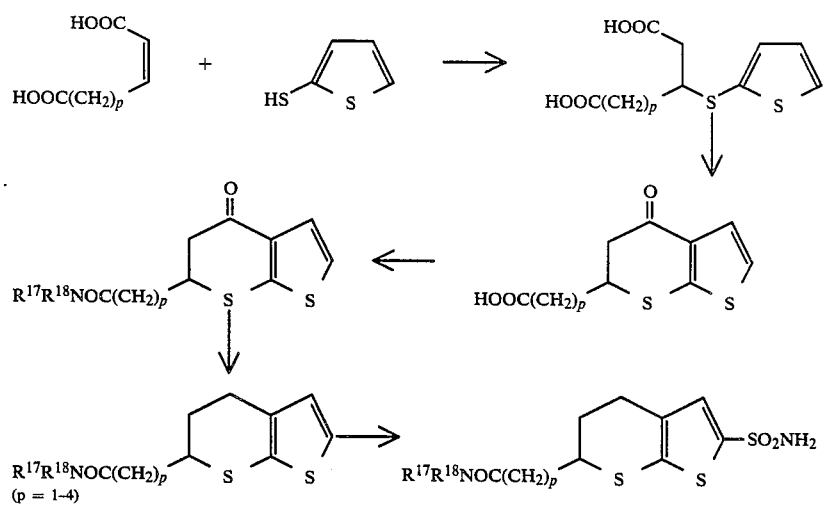

TABLE VIII

| P | R$^{17}$ | R$^{18}$ |
|---|---|---|
| 2 | —CH₃ | —CH₃ |
| 3 | —CH₃ | —CH₃ |
| 4 | —CH₃ | —CH₃ |
| 5 | —CH₃ | —CH₃ |
| 2 | —CH₃ | —CH₃ |
| 3 | —C₂H₅ | H |
| 4 | —C₂H₅ | H |
| 5 | —C₂H₅ | H | matographed on silica gel using 10% methanol/chloroform and the 6-methylene analog was obtained as a colorless gum (0.30 g). The remaining fractions from the chromatography were the 6-dimethylaminomethyl-7-oxide and 7,7-dioxide analogs.

Employing the procedure substantially as described in Example 22, but substituting for the dimethylaminomethyl compound used therin the aminoalkyl-thio compounds described in Table IX there are produced the sulfones also described in Table IX in accordance with the following reaction:

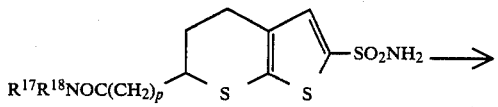

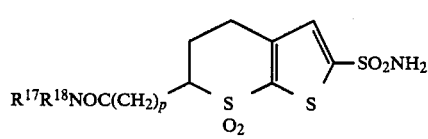

TABLE IX

| P | R$^{17}$ | R$^{18}$ |
|---|---|---|
| 2 | —CH$_3$ | —CH$_3$ |
| 3 | —CH$_3$ | —CH$_3$ |
| 4 | —CH$_3$ | —CH$_3$ |
| 5 | —CH$_3$ | —CH$_3$ |
| 2 | —CH$_3$ | —CH$_3$ |
| 3 | —C$_2$H$_5$ | H |
| 4 | —C$_2$H$_5$ | H |
| 5 | —C$_2$H$_5$ | H |
| 2 | —CH$_2$CH$_3$ | H |
| 2 | —CH(CH$_3$)$_2$ | —CH$_3$ |
| 3 | —CH$_2$CH(CH$_3$)$_2$ | H |
| 4 | —CH$_2$CH(CH$_3$)$_2$ | —CH$_3$ |
| 2 | —CH$_2$CH$_2$—O—CH$_2$CH$_2$— | |
| 2 | —CH$_2$CH$_2$—CH$_2$—CH$_2$CH$_2$— | |
| 2 | —CH$_2$CH$_2$—CH$_2$CH$_2$— | |
| 2 | —CH$_2$CH$_2$—N—CH$_2$—CH$_2$<br>                             CH$_3$ | |
| 2 | —CH$_2$—⊲ | H |

EXAMPLE 23

5,6-Dihydro-6-(2-methylpropylaminomethyl)-4H-thieno-[2,3-b]thiopyran-2-sulfonamide-7,7-dioxide hydrochloride 5,6-Dihydro-6-methylene-4H-thieno[2,3-b]thiopyran-2-sulfonamide-7,7-dioxide (0.58 g, 0.0021 mol) was dissolved in methanol (2½ ml) and isobutylamine (0.29 g, 0.004 mol) was added. The solution was stirred at room temperature overnight. The solvent was removed in vacuo and the crude oily residue was chromatographed on silica gel (50 g) using 5% methanol-chloroform. A white solid was recovered (0.44 g), m.p. 130.5°–133° C. The hydrochloride salt was prepared using ethanolic-HCl and ether to give 0.42 g of white solid hydrochloride salt, m.p. 250°–252° C.

Following the procedure substantially as described in Example 23, but using the amines depicted in Table XI, there are produced the 6-substituted aminomethyl compounds also depicted in the table by the following reaction scheme:

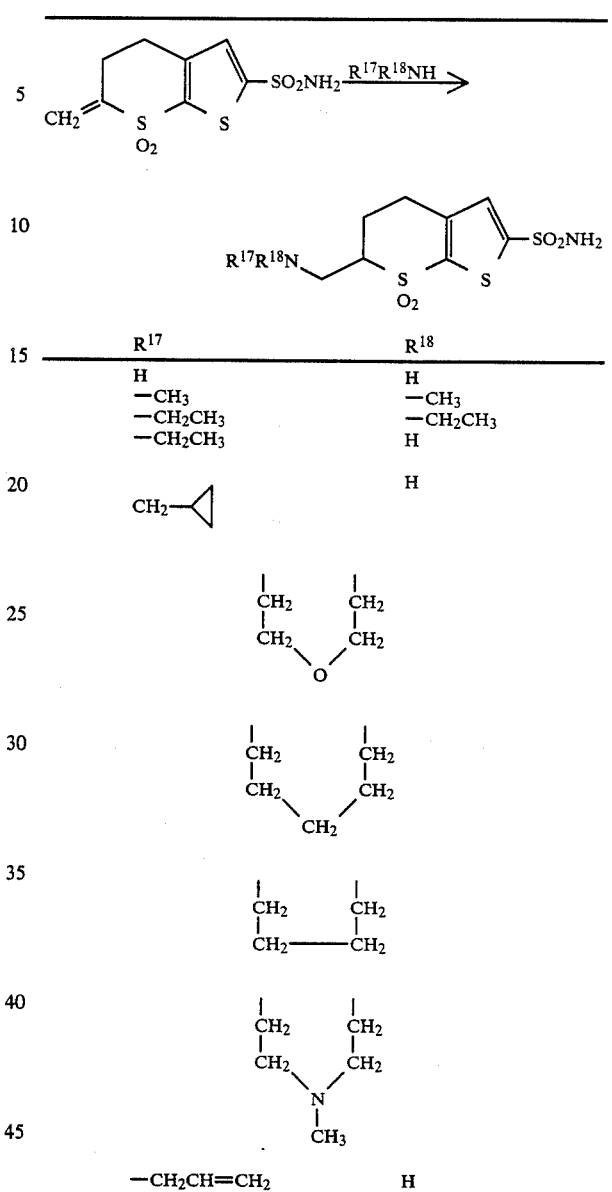

EXAMPLE 24

Resolution of trans-5,6-dihydro-4H-4-ethylamino-6-methylthieno[2,3-b]thiopyran-2-sulfonamide-7,7-dioxide

Step A

A mixture of the title compound (2.8 g, 0.0086 mol) and a di-p-toluoyl-D-tartaric acid monohydrate (0.85 g, 0.0021 mol) in n-propanol (300 ml) was heated to boiling and the hot solution filtered through a filter-aid pad with a layer of charcoal (Norite and Darco). The filtrate was concentrated by boiling to a volume of about 75 ml and then allowed to crystallize. After standing overnight, the crystals were filtered off and the material recrystallized twice more from n-propanol (~75 ml) to yield a 2:1 salt of free base to acid. The combined mother liquors from these recrystallization were saved for Step B. The salt was then treated with a saturated solution of NaHCO$_3$ and the mixture extracted with ethyl acetate (5 x). The organic extracts were dried, filtered and concentrated to dryness to yield 0.6 g of free base. The hydrochloride salt was prepared from 5.6N HCl ethanol and crystallized from CH$_3$OH-isopropanol to yield 0.53 g of the (+) isomer; $[\alpha]_D^{24} = 8.23$ (C, 0.9CH$_3$OH); m.p. 283°–285° C.

Step B

The combined mother liquors from Step A were treated with a saturated solution of NaHCO$_3$ and the mixture extracted with ethyl acetate (5 x). The organic extracts were dried, filtered and concentrated to dryness. The residue was treated with di-p-toluoyl-L-tartaric acid monohydrate (0.85, 0.0021 mol) and n-propanol (200 ml) and the isomers separated by the process described in Step A to give 0.7 g of the (−) isomer; $[\alpha]_D^{24} = -8.34$ (C, 1.0CH$_3$OH); m.p. 283°–285° C.

EXAMPLE 25

5,6-Dihydro-6,6-dimethyl-4-hydroxy-5-((2-methylpropylamino)methyl)-4H-thieno[2,3-b]thiopyran-2-sulfonamide-7,7-dioxide hydrochloride hydrate

Step A: Preparation of N'-(5,6-Dihydro-6,6-dimethyl(-4H-4-oxo-thieno[2,3-b]thiopyran-2-sulfonyl)-NN-dimethylformamidine)sulfonamide A solution of 5,6-dihydro-6,6-dimethyl-4H-4-oxo-thieno[2,3-b]thiopyran-2-sulfonamide (17 g) in acetonitrile (500 ml) was stirred in an ice bath and treated with dimethylformamide dimethylacetal (9 ml). Stirring was continued for 2 hours at 25° C., the acetonitrile was evaporated in vacuo and the residue was crystallized from ethyl acetate (150 ml)-hexane (50 ml) to give 12 g of product; m.p. 122°–124° C.

Analysis Calc'd for C$_{17}$H$_{16}$N$_2$O$_3$S$_3$: C, 43.35; H, 4.85; N, 8.43. C, 43.27; H, 5.27; N, 8.64.

Step B: Preparation of N'-(5,6-Dihydro-6,6-dimethyl-4H-5-methylene-4-oxo-thieno[2,3-b]thiopyran-2-sulfonyl)N,N-dimethylformamidine A mixture of producrt from Step A (5.35 g), paraformaldehyde (1.7 g), dimethylamine hydrochloride (9 g) and acetic acid (2 ml) was stirred on a steam bath for 3 hours. To the 5-dimethylaminomethyl intermediate thus formed was added dimethylformamide and heating was continued for 1 hour. The reaction mixture was poured into ice H$_2$O to give the product as a white solid; m.p. 118°–120° C. after recrystallization from 2-propanol-H$_2$O.

Analysis Clac'd for C$_{13}$H$_{16}$N$_2$O$_3$S$_3$: C, 45.33; H, 4.68; N, 8.13. Found: C, 45.65, H, 4.83; N, 7.84.

Step C: Preparation of 5,6-Dihydro-6,6-dimethyl-4H-2-methylene-4-oxo-thieno[2,3-b]thiopyran-2-sulfonamide A stirred solution of product from Step B (11.5 g), THF (300 ml) and 6NHCl (150 ml) was heated at reflux for 6 hours. The THF was evaporated in vacuo, the crude product was collected on a filter, stirred in 2-propanol for 20 minutes filtered and dried to give 4.6 g of product; m.p. 154°–156° C.

Analysis Calc'd for C$_{10}$H$_{11}$NO$_3$S$_3$: C, 41.50; H, 3.83; N, 4.84. Found: C, 41.69; H, 3.80; N, 5.03.

Step D: Preparation of 5,6-Dihydro-6,6-dimethyl-5-((2-methylpropylamino)methyl)-4H-4-oxothieno[2,3-b]thiopyran-2-sulfonamide hydrochloride A mixture of product from Step C (0.4 g), isobutylamine (2 ml) and alumina (III) (0.7 g) in benzene (15 ml) was stirred at 25° C. for 1 hour filtered and the benzene evaporated in vacuo. The residue was treated with H$_2$O (25 ml), a slight excess of HCl then a slight excess of sodium bicarbonate, and extracted with ethylacetate which was washed with water, dried over MgSO$_4$ and evaporated in vacuo. The residue was dissolved in ethanol (3 ml) treated with a slight excess of ethanolic HCl (10N) then poured into ether (60 ml). The product which separated was collected on a filter and dried.

Analysis Calc'd for C$_{14}$H$_{22}$N$_2$O$_3$S$_2$·HCl C, 42.14, H, 5.81; N, 7.02. Found: C, 42.42; H, 6.09; N, 7.02.

Step E: Preparation of 5,6-Dihydro-6,6-dimethyl-4-hydroxy-5-((2-methylpropylamino)methyl)-4H-thieno[2,3-b]thiopyran-2-sulfonamide-7,7-dioxide hydrochloride hydrate To a solution of product from Step D (1.1 g) in methanol (50 ml) was added sodium borhydride (136 mg) over a 5 minute period. After stirring for 1 hour a solution of Oxone (2.51 g) in H$_2$O (15 ml) was added over 10 minutes and stirring was continued overnight. The methanol was evaporated in vacuo and the aqueous residue was treated with an excess of sodium bicarbonate, extracted with ethylacetate, washed with H$_2$O, dried over MgSO$_4$ and evaporated in vacuo. The residue was purified by chromatography on silica gel (40 g) eluting with CHCl$_3$—CH$_3$OH (4:1). The pertinent fractions were evaporated, the residue was dissolved in ethanol (4 ml), treated with ethanolic HCl and poured into 100 ml of ether. The product which separated was filtered and dried.

Analysis Calc'd for C$_{14}$H$_{24}$N$_2$O$_5$S$_3$·HCl·H$_2$O C, 37.28; H, 6.03; N, 6.21. Found: C, 37.20; H, 5.94; N, 6.08.

EXAMPLE 26

| | | |
|---|---|---|
| 5,6-dihydro-4H—6-(4-hydroxy-3-dimethylaminomethylphenyl)-thieno[2,3-b]thiopyran-2-sulfonamide-7,7-dioxide | 1 mg | 15 mg |
| Monobasic sodium phosphate 2H$_2$O | 9.38 mg | 6.10 mg |
| Dibasic sodium phosphate .12H$_2$O | 28.48 mg | 16.80 mg |
| Benzalkonium chloride | 0.10 mg | 0.10 mg |
| Water for injection q.s. and. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 27

| | |
|---|---|
| 5,6-dihydro-4H—6-(4-hydroxy-3-dimethylaminomethylphenyl)-thieno[2,3-b]thiopyran-2-sulfonamide-7,7-dioxide | 5 mg |
| petrolatum q.s. and. | 1 gram |

The compound and the petrolatum are aseptically combined.

EXAMPLE 28

| | |
|---|---|
| 5,6-dihydro-4H—6-(4-hydroxy-3-dimethylaminomethylphenyl)-thieno[2,3-b]thiopyran-2-sulfonamide-7,7-dioxide | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

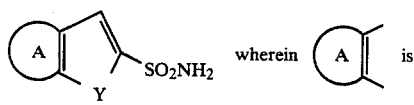

wherein 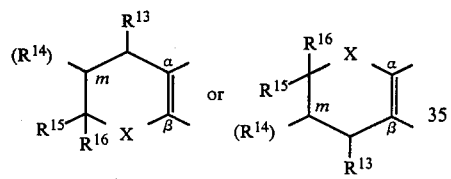 is or a pharmacologically acceptable salt thereof, wherein:

X is —S—, —SO—, or —SO$_2$—;
Y is —S—, C$_{1-3}$alkyl or benzyl,
m is 1
R$^{13}$ is
  (a) hydrogen,
  (b) phenyl either unsubstituted or substituted with one or more of
    (1) hydroxy,
    (2) C$_{1-3}$alkoxy,
    (3) R$^{17}$R$^{18}$N-C$_{1-5}$alkyl, wherein R$^{17}$ and R$^{18}$ are independently selected from:
      (i) hydrogen or
      (ii) C$_{1-5}$alkyl, or taken together with the nitrogen to which they are attached form a heterocycle selected from morpholine, piperidine, pyrrolidine, and piperazine,
  (c) —OH,
  (d) =O; or
  (e) —NR$^{17}$R$^{18}$
R$^{14}$ is
  (a) hydrogen,
  (b) —CN,
  (c) phenyl-C$_{1-3}$alkyl, wherein the phenyl is either unsubstituted or substituted with one or more of
    (1) hydroxy,
    (2) C$_{1-3}$alkoxy, or
    (3) R$^{17}$R$^{18}$N-C$_{1-5}$alkyl;
R$^{15}$ is
  (a) hydrogen,
  (b) C$_{1-5}$alkyl,
  (c) phenyl-C$_{1-3}$alkyl, wherein the phenyl is either unsubstituted or substituted with on or more of:
    (1) hydroxy,
    (2) C$_{1-3}$alkoxy,
    (3) R$^{17}$R$^{18}$N-C$_{1-3}$alkyl,
  (d) phenyl either unsubstituted or substituted with one or more of
    (1) hydroxy,
    (2) C$_{1-3}$alkoxy,
    (3) R$^{17}$R$^{18}$N-C$_{1-3}$alkyl, or
    (4) chloro or fluoro
  (e) aromatic heterocycle of 5 or 6 members selected from furyl, pyridyl, and thienyl either unsubstituted or substituted with R$^{17}$R$^{18}$N-C$_{1-3}$alkyl,
  (f) —NR$^{17}$R$^{18}$; and
  (g) C$_{2-5}$alkyl substituted with —NR$^{17}$R$^{18}$
R$^{16}$ is
  (a) hydrogen, or
  (b) C$_{1-3}$alkyl, with the proviso that if R$^{13}$ is other than phenyl or substituted phenyl and R$^{14}$ is hydrogen, one of R$^{15}$ and R$^{16}$ is other than hydrogen.

2. The compound of claim 1, wherein X is —SO$_2$—, R$^{13}$ is H or —NR$^{17}$R$^{18}$, R$^{14}$ is hydrogen, R$^{16}$ is hydrogen or C$_{1-3}$ alkyl and R$^{15}$ is C$_{1-5}$ alkyl, C$_{2-5}$alkyl substituted with R$^{17}$R$^{18}$—N—, or phenyl substituted with hydroxy and/or R$^{17}$R$^{18}$N-C$_{1-3}$ alkyl.

3. The compound of claim 2 wherein R$^{15}$ is phenyl substituted with —OH and/or R$^{17}$R$^{18}$N-C$_{1-3}$alkyl.

4. The compound of claim 2, of structural formula:

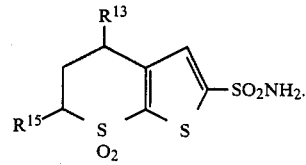

5. The compound of Claim 3, of structural formula:

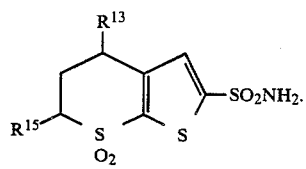

6. The compound
5,6,-dihydro-4-ethylamino-6-methyl-4H-thieno[2,3-b]thiopyran-2-sulfonamide-7,7-dioxide and its (−)-trans-enantiomer;

5,6-dihydro-4-(2-methylpropylamino)-6-methyl-4H-thieno[2,3-b]thiopyran-2-sulfonamide-7,7-dioxide and its (−)-trans-enantiomer;

5,6-dihydro-6,6-dimethyl-4-ethylamino-4H-thieno[2,3-b]thiopyran-2-sulfonamide-7,7-dioxide;

5,6-dihydro-5-(3-dimethylaminomethyl-4-hydroxybenzyl)-4H-thieno[2,3-b]thiopyran-2-sulfonamide-7,7-dioxide;

5,6-dihydro-6-(3-dimethylaminomethyl-4-hydroxyphenyl)-4H-thieno[2,3-b]thiopyran-2-sulfonamide-7,7-dioxide; or 5,6-dihydro-6-(ethylaminoethyl)-4H-thieno[2,3-b]thiopyran-2-sulfonamide-7,7-dioxide.

7. The compound (−)-trans-5,6-dihydro-4-ethylamino-6-methyl-4H-thieno[2,3-b]thiopyran-2-sulfonamide-7,7-dioxide.

8. An ophthalmological formulation for the treatment of ocular hypertension comprising an ophthalmologically acceptable carrier and an effective ocular antihypertensive amount of a compound of claim 1.

9. An ophthalmological formulation for the treatment of ocular hypertension comprising an ophthalmologically acceptable carrier and an effective ocular antihypertensive amount of the compound of claim 6.

10. An ophthalmological formulation for the treatment of ocular hypertension comprising an ophthalmologically accetable carrier and an effective ocular antihypertensive amount of the compound of claim 7.

11. A method of treating ocular hypertension comprising topical ocular administration to a patient in need of such treatment of an effective ocular antihypertensive amount of a compound of claim 1.

12. A method of treating ocular hypertension comprising topical ocular administration to a patient in need of such treatment of an effective ocular antihypertensive amount of the compound of claim 6.

13. A method of treating ocular hypertension comprising topical ocular administration to a patient in need of such treatment of an effective ocular antihypertensive amount of the compound of claim 7.

* * * * *

UNITED STATES PATENT AND TRADEMARK OFFICE

CERTIFICATE EXTENDING PATENT TERM
UNDER 35 U.S.C. § 156

PATENT NO.     :   4,797,413

ISSUED         :   January 10, 1989

INVENTOR(S)    :   John J. Baldwin et al.

PATENT OWNER   :   Merck & Co., Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,233 days from the original expiration date of the patent, December 12, 2004, with all rights pertaining thereto as provided by 35 U.S.C. § 156(b).

I have caused the seal of the Patent and Trademark Office to be affixed this 21st day of April 1997.

Bruce A. Lehman
Assistant Secretary of Commerce and
Commissioner of Patents and Trademarks

REEXAMINATION CERTIFICATE (1852nd)
United States Patent [19]
Baldwin et al.

[11] B1 4,797,413
[45] Certificate Issued Nov. 24, 1992

[54] THIENO THIOPYRAN SULFONAMIDE DERIVATIVES PHARMACEUTICAL COMPOSITIONS AND USE

[75] Inventors: John J. Baldwin, Gwynedd Valley; Gerald S. Ponticello, Lansdale; Marcia E. Christy, Collegeville, all of Pa.

[73] Assignee: Merck & Co., Inc., Rahway, N.J.

Reexamination Request:
No. 90/002,682, Mar. 23, 1992

Reexamination Certificate for:
Patent No.: 4,797,413
Issued: Jan. 10, 1989
Appl. No.: 67,326
Filed: Jun. 26, 1987

Related U.S. Application Data

[63] Continuation-in-part of Ser. No. 863,225, May 14, 1986, Pat. No. 4,677,115, which is a continuation-in-part of Ser. No. 777,654, Sep. 19, 1985, abandoned, which is a continuation-in-part of Ser. No. 680,684, Dec. 12, 1984, abandoned.

[51] Int. Cl.$^5$ .................. A61K 31/38; A61K 31/535; C07D 495/04
[52] U.S. Cl. ............................ 514/432; 514/232.5; 514/233.8; 514/253; 514/316; 514/318; 514/331; 514/338; 514/422; 514/913; 544/79; 544/121; 544/130; 544/131; 544/141; 544/145; 544/146; 544/357; 544/364; 544/372; 544/377; 546/187; 546/193; 546/194; 546/197; 546/220; 548/523; 548/526; 549/23

[56] References Cited

U.S. PATENT DOCUMENTS 4,619,939 10/1986 Maren ................................ 514/363

FOREIGN PATENT DOCUMENTS 0189690 8/1986 European Pat. Off. .

Primary Examiner—R. W. Ramsuer

[57] ABSTRACT

Aromatic sulfonamides with a saturated heterocycle fused thereto are carbonic anhydrase inhibitors useful in the treatment of elevated intraocular pressure.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-13 is confirmed.

* * * * *